United States Patent
Lallemand et al.

(10) Patent No.: US 11,905,545 B2
(45) Date of Patent: *Feb. 20, 2024

(54) METHOD FOR IDENTIFYING YEAST OR BACTERIA FROM A LUMINOUS INTENSITY REFLECTED BY, OR TRANSMITTED THROUGH, AN ILLUMINATED MICROORGANISM

(71) Applicant: BIOMERIEUX, Marcy l'Etoile (FR)

(72) Inventors: Jordane Lallemand, Villeneuve les Maguelone (FR); Denis Leroux, Trevoux (FR); Manuel Petit, Grenoble (FR)

(73) Assignee: BIOMERIEUX, Marcy l'Etolle (FR)

( * ) Notice: Subject to any disclaimer, the term of this patent is extended or adjusted under 35 U.S.C. 154(b) by 405 days.

This patent is subject to a terminal disclaimer.

(21) Appl. No.: 16/772,410

(22) PCT Filed: Dec. 20, 2018

(86) PCT No.: PCT/FR2018/053436
§ 371 (c)(1),
(2) Date: Jun. 12, 2020

(87) PCT Pub. No.: WO2019/122734
PCT Pub. Date: Jun. 27, 2019

(65) Prior Publication Data
US 2021/0079442 A1 Mar. 18, 2021

(30) Foreign Application Priority Data
Dec. 21, 2017 (FR) ...................................... 1762828

(51) Int. Cl.
*C12Q 1/04* (2006.01)
*G01N 21/3563* (2014.01)
(Continued)

(52) U.S. Cl.
CPC ............... *C12Q 1/04* (2013.01); *G01N 21/31* (2013.01); *G01N 21/359* (2013.01); *G01N 21/3563* (2013.01)

(58) Field of Classification Search
CPC .... C12Q 1/04; G01N 21/3563; G01N 21/359; G01N 21/31
See application file for complete search history.

(56) References Cited

U.S. PATENT DOCUMENTS 4,512,660 A * 4/1985 Goldberg ................. G01J 3/44
356/301
5,510,246 A * 4/1996 Morgan ................. C12M 41/36
435/808
(Continued)

FOREIGN PATENT DOCUMENTS

EP 3257947 A1 12/2017
JP 2001-272399 A 10/2001
(Continued)

OTHER PUBLICATIONS

International Search Report and Written Opinion dated Mar. 21, 2019 in counterpart application No. PCT/FR2018/053436 (with English partial translation and partial machine translation; total 28 pages).

(Continued)

*Primary Examiner* — Michael P LaPage
(74) *Attorney, Agent, or Firm* — Seckel IP, PLLC

(57) ABSTRACT

Method for characterising a microorganism, comprising: —illuminating, in the wavelength range of 390 nm-900 nm, the microorganism having a natural electromagnetic response in said range; —acquiring, in said range, a light intensity reflected by said (or transmitted through said) illuminated microorganism; and —determining the micro- (Continued)

organism as being a yeast or a bacterial strain according to the light intensity acquired in said range.

25 Claims, 19 Drawing Sheets

(51) Int. Cl.
    *G01N 21/359*     (2014.01)
    *G01N 21/31*     (2006.01)

(56) References Cited

U.S. PATENT DOCUMENTS

| | | | |
|---|---|---|---|
| 8,652,800 | B2 | 2/2014 | Walsh et al. |
| 8,748,122 | B2 | 6/2014 | Hyman et al. |
| 8,795,983 | B2 | 8/2014 | Hyman et al. |
| 9,822,389 | B2 | 11/2017 | Hyman et al. |
| 2003/0082516 | A1* | 5/2003 | Straus .............. G01N 33/56938 435/287.1 |
| 2007/0279629 | A1* | 12/2007 | Grun ...................... G01N 21/65 356/318 |
| 2009/0303472 | A1* | 12/2009 | Zhao ................ G01N 33/56916 356/301 |
| 2010/0014078 | A1* | 1/2010 | Dholakia ................... G01J 3/28 356/301 |
| 2010/0068755 | A1 | 3/2010 | Walsh et al. |
| 2010/0129858 | A1 | 5/2010 | Walsh et al. |
| 2010/0136609 | A1* | 6/2010 | Clay ...................... G01N 21/65 435/29 |
| 2010/0288060 | A1 | 11/2010 | Ronsick et al. |
| 2011/0033847 | A1 | 2/2011 | Hyman et al. |
| 2011/0281291 | A1* | 11/2011 | Ullery ...................... G16B 40/20 250/282 |
| 2012/0135454 | A1 | 5/2012 | Walsh et al. |
| 2013/0323718 | A1 | 12/2013 | Hyman et al. |
| 2014/0335558 | A1 | 11/2014 | Hyman et al. |
| 2014/0377795 | A1 | 12/2014 | Gannot et al. |
| 2017/0073725 | A1 | 3/2017 | Upton et al. |
| 2017/0236281 | A1* | 8/2017 | Dacosta ............... A61B 5/0071 382/128 |
| 2018/0128747 | A1* | 5/2018 | Zhao ..................... G01N 21/274 |
| 2018/0245124 | A1 | 8/2018 | Bork |
| 2019/0195802 | A1* | 6/2019 | Attar ..................... G01N 33/493 |
| 2019/0293620 | A1* | 9/2019 | Farkas .................... G01N 21/65 |
| 2019/0323948 | A1 | 10/2019 | Leroux et al. |
| 2021/0079441 | A1 | 3/2021 | Lallemand et al. |

FOREIGN PATENT DOCUMENTS

| | | |
|---|---|---|
| JP | 2011-529187 A | 12/2011 |
| JP | 2015-507182 A | 3/2015 |
| KR | 20110091717 A | 8/2011 |
| WO | 2010011798 A1 | 1/2010 |
| WO | 2010077304 A2 | 7/2010 |
| WO | 2010132823 A2 | 11/2010 |
| WO | 2016137341 A1 | 9/2016 |

OTHER PUBLICATIONS

J.D. Walsh et al., "Rapid Intrinsic Fluorescence Method for Direct Identification of Pathogens in Blood Cultures", mBio, vol. 4, No. 6, Nov. 19, 2013, e00865-13, pp. 1-9 (in English; D1 cited in the ISR).
International Search Report and Written Opinion dated Apr. 26, 2019 of application No. PCT/FR2018/053434 corresponding to co-pending U.S. Appl. No. 16/772,402 (with English partial translation and partial machine translation; total 22 pages) (Note: US20170236281, D1 cited in the ISR is not listed in this IDS since it is already of record in this application).
H.S. Kim et al., "Development of a multispectral light-scatter sensor for bacterial colonies", Journal of Biophotonics, vol. 10, No. 5, Jul. 14, 2016, pp. 634-644 (in English; D2 cited in the ISR of co-pending U.S. Appl. No. 16/772,402).
M. Guillemot et al., "Hyperspectral imaging for presumptive identification of bacterial colonies on solid chromogenic culture media", Proceedings of SPIE, SPIE, Bellingham, WA, vol. 9887, Apr. 27, 206, pp. 98873L-1 to 98873L-12 (total 12 pages) in English; D3 cited in the ISR of co-pending U.S. Appl. No. 16/772,402).
S. Arrigoni et al., "Hyperspectral image analysis for rapid and accurate discrimination of bacterial infections: A benchmark study", Computers in Biology and Medicine, vol. 88, Jun. 21, 2017, pp. 60-71 (in English; D4 cited in the ISR of co-pending U.S. Appl. No. 16/772,402).
M. Graus et al., "Hyperspectral fluorescence microscopy detects autofluorescent factors that can be exploited as a diagnostic method for species differentiation", Journal of Biomedical Optics, vol. 22, No. 1, Jan. 2017, cover page and pp. 016002-1 to 016002-6 (total 7 pages) (in English; D5 cited in the ISR of co-pending U.S. Appl. No. 16/772,402).
B. Park et al., "Hyperspectral microscope imaging methods to classify grampositive and gram-negative foodborne pathogenic bacteria", Transactions of the ASABE, American Society of Agricultural and Biological Engineers, St. Joseph, MI, vol. 58, No. 1, Jan. 1, 2015, pp. 5-16 (in English; D6 cited in the ISR of co-pending U.S. Appl. No. 16/772,402).
Notice of Allowance dated Jun. 30, 2022 in co-pending U.S. Appl. No. 16.772,402 (with PTO892, without returned SB08; total 9 pages).
Tshikhudo, "Bacterial species identification getting easier", African Journal of Biotechnology, vol. 12, No. 41, pp. 5975-5982, Oct. 9, 2013 (Note: ref.U cited in the Notice of Allowance dated Jun. 30, 2022 in co-pending U.S. Appl. No. 16/772,402).
Japanese Office Action dated Oct. 4, 2022 in counterpart application JP 2020-533199 (with English translation; total 10 pages) (Note: Walsh et al. 2013, D3; Arrigoni et al 2017, D6; and Guillemot 2016, D7 cited in this JP Office Action are not listed in this IDS form since they are already of record or listed in IDS forms filed concurrently).
Turra et al., "Hyperspectral image acquisition and analysis of cultured bacteria for the discrimination of urinary tract infections", 2015 37th Annual International Conference of the IEEE Engineering in Medicine and Biology Society (EMBC), 2015, pp. 759-762 (Note: in English; D1 cited in the JP Office Action dated Oct. 4, 2022).
Japanese Office Action dated Oct. 4, 2022 in application JP 2020-533214, counterpart of co-pending U.S. Appl. No. 16/772,402 (with English translation; total 8 pages) (Note: D1-D7 cited in this JP Office Action are D6, D2-D5, D1, and D7 cited in the JP Office Action dated Oct. 4, 2022 in counterpart application JP 2020-533199).
Korean Office Action dated Jun. 21, 2023 in counterpart application KR 10-2020-7021137 (with English translation; total 15 pages) (Note: Turra et al., D2 cited in the KR Office Action is not listed in this IDS form since it was already listed as NPL2 in the IDS filed Nov. 23, 2022).
Korean Office Action dated Jun. 21, 2023 in application KR 10-2020-7021133, counterpart of co-pending U.S. Appl. No. 16/772,402 (with English translation; total 17 pages) (Note: Turra et al., D2 cited in the KR Office Action is not listed in this IDS form since it was already listed in the IDS filed Nov. 23, 2022).
CN Office Action dated Nov. 11, 2023 in counterpart application No. CN 201880082224.8 (with English translation; total 17 pages) (note: D1, EP3257947A1 and D2, US20140377795A1 cited in the CN Office Action are not listed in this IDS since they are already of record in this application).
CN Office Action dated Sep. 26, 2023 in application No. CN 201880082258.7, counterpart of co-pending U.S. Appl. No. 16/772,402 (with English machine translation; total 16 pages) (note: D1, EP3257947A1, D2, US20140377795A1, and D6, US20100068755 cited in the CN Office Action are not listed in this IDS since they are already of record in this application; D3, US2017073725 is already listed on the IDS.

* cited by examiner

| Species | Vitek code | Class |
|---|---|---|
| *Citrobacter koseri* | CIT-KOS | GNF |
| *Enterobacter cloacae* | ENT-CLC | GNF |
| *Escherichia coli* | ESH-COL | GNF |
| *Klebsiella pneumoniae* | KLB-PEU | GNF |
| *Morganella morganii* | MOR-MOR | GNF |
| *Enterococcus faecalis* | ENC-FAE | GP |
| *Staphylococcus aureus* | STA-AUR | GP |
| *Staphylococcus epidermidis* | STA-EPI | GP |
| *Streptococcus agalactiae* | STR-AGA | GP |
| *Streptococcus pyogenes* | STR-PYO | GP |
| *Streptococcus viridans (mitis)* | STR-MIT | GP |
| *Candida albicans* | CAN-ALB | Y |
| *Candida guilliermondii* | CAN-GUI | Y |
| *Candida lusitaniae* | CAN-LUS | Y |
| *Candida tropicalis* | CAN-TRO | Y |
| *Candida parapsilosis* | CAN-PRP | Y |
| *Candida dubliniensis* | CAN-DBL | Y |
| *Candida lusitaniae* | CAN-LUS | Y |
| *Burkholderia cepacia* | BUR-CEP | GNNF |
| *Pseudomonas aeruginosa* | PSD-AEU | GNNF |
| *Stenotrophomonas maltophilia* | STE-MLT | GNNF |

Figure 8

| Species | COS medium | | | |
|---|---|---|---|---|
| | Block 1 | | Block 2 | |
| | Number of colonies | Number of pixels | Number of colonies | Number of pixels |
| ACN-BAU | 20 | 1777 | 19 | 1892 |
| ALC-FAE | 2 | 106 | 2 | 92 |
| BUR-CEP | 27 | 810 | 28 | 630 |
| CAN-ALB | 30 | 1525 | 29 | 1255 |
| CAN-DBL | 28 | 1423 | 27 | 1550 |
| CAN-GUI | 51 | 2832 | 51 | 2887 |
| CAN-KEF | 26 | 3434 | 26 | 3830 |
| CAN-KRU | 11 | 855 | 11 | 806 |
| CAN-LUS | 25 | 1556 | 25 | 1581 |
| CAN-PRP | 29 | 1936 | 28 | 2184 |
| CAN-TRO | 21 | 2379 | 21 | 2358 |
| CIT-KOS | 19 | 3135 | 19 | 3316 |
| ENC-FAE | 59 | 4467 | 59 | 4527 |
| ENT-CLC | 9 | 1635 | 9 | 1696 |
| ESH-COL | 10 | 1424 | 10 | 1936 |
| KLB-PEU | 6 | 3238 | 5 | 3143 |
| MOR-MOR | 5 | 4549 | 5 | 2360 |
| PSD-AEU | 11 | 2035 | 10 | 2284 |
| STA-AUR | 15 | 1458 | 14 | 1402 |
| STA-EPI | 17 | 964 | 16 | 730 |
| STE-MLT | 21 | 1686 | 20 | 1684 |
| STR-AGA | 54 | 2264 | 53 | 1758 |
| STR-MIT | 49 | 1531 | 49 | 1616 |
| STR-PYO | 77 | 1548 | 76 | 1654 |
| TOTAL | 622 | 48567 | 618 | 47171 |

Figure 9

| Species | TSA medium | | | |
|---|---|---|---|---|
| | Block 1 | | Block 2 | |
| | Number of colonies | Number of pixels | Number of colonies | Number of pixels |
| ACN-BAU | 8 | 542 | 7 | 476 |
| ALC-FAE | 2 | 73 | 2 | 76 |
| BUR-CEP | 14 | 418 | 13 | 373 |
| CAN-ALB | 6 | 623 | 5 | 529 |
| CAN-DBL | 6 | 390 | 5 | 372 |
| CAN-GUI | 23 | 2102 | 22 | 2191 |
| CAN-KEF | 14 | 2382 | 14 | 1676 |
| CAN-KRU | 33 | 807 | 32 | 775 |
| CAN-LUS | 24 | 2140 | 24 | 2074 |
| CAN-PRP | 21 | 1454 | 20 | 1083 |
| CAN-TRO | 6 | 1457 | 5 | 1378 |
| CIT-KOS | 8 | 1816 | 8 | 1976 |
| ENC-FAE | 36 | 1297 | 35 | 1448 |
| ENT-CLC | 24 | 3129 | 24 | 2455 |
| ESH-COL | 2 | 251 | 2 | 390 |
| KLB-PEU | 2 | 2144 | 1 | 1220 |
| MOR-MOR | 7 | 1151 | 7 | 1359 |
| PSD-AEU | 3 | 355 | 3 | 414 |
| STA-AUR | 23 | 1619 | 22 | 1298 |
| STA-EPI | | | | |
| STE-MLT | 22 | 894 | 21 | 1078 |
| STR-AGA | 12 | 831 | 12 | 702 |
| STR-MIT | 8 | 140 | 7 | 125 |
| STR-PYO | 24 | 1121 | 23 | 950 |
| TOTAL | 328 | 27136 | 314 | 24418 |

Figure 10

| | | Class predicted | | | | TOTAL | Sensitivity |
|---|---|---|---|---|---|---|---|
| | | A | B | C | D | | |
| Actual class | A | $n_{AA}$ | $n_{AB}$ | $n_{AC}$ | $n_{AD}$ | $n_{A\cdot}$ | $n_{AA}/n_{A\cdot}$ |
| | B | $n_{BA}$ | $n_{BB}$ | $n_{BC}$ | $n_{BD}$ | $n_{B\cdot}$ | $n_{BB}/n_{B\cdot}$ |
| | C | $n_{CA}$ | $n_{CB}$ | $n_{CC}$ | $n_{CD}$ | $n_{C\cdot}$ | $n_{CC}/n_{C\cdot}$ |
| | D | $n_{DA}$ | $n_{DB}$ | $n_{DC}$ | $n_{DD}$ | $n_{D\cdot}$ | $n_{DD}/n_{D\cdot}$ |
| | TOTAL | $n_{\cdot A}$ | $n_{\cdot B}$ | $n_{\cdot C}$ | $n_{\cdot D}$ | $n_{\cdot\cdot}$ | |
| | Specificity | $n_{AA}/n_{\cdot A}$ | $n_{BB}/n_{\cdot B}$ | $n_{CC}/n_{\cdot C}$ | $n_{DD}/n_{\cdot D}$ | | |

Figure 11

$n_{AA}$ : Set of samples of Class A properly classified in A by the model (TP)
$n_{AB}$ : Set of samples of Class A wrongly classified in B by the model (FN)
$n_{BA}$ : Set of samples of Class B wrongly classified in A by the model (FP)
$n_{A\cdot}$ : Set of samples of Class A
$n_{\cdot A}$ : Set of samples classified in A by the model
$n_{\cdot\cdot}$ : Complete set $$CR = \frac{n_{AA}+n_{BB}+n_{CC}+n_{DD}}{n_{\cdot\cdot}} \qquad BCR = \frac{(n_{AA}/n_{A\cdot})+(n_{BB}/n_{B\cdot})+(n_{CC}/n_{C\cdot})+(n_{DD}/n_{D\cdot})}{4} = \frac{\Sigma(n_{ii}/n_{i\cdot})}{4}$$

| | Branch 1: "GNF" versus "GP+GNN+Y" | | | | Branch 2: "GP" versus "GNN+Y" | | | | Branch 3: "GNN" versus "Y" | | |
|---|---|---|---|---|---|---|---|---|---|---|---|
| | | BCR (in %) | | | | BCR (in %) | | | | BCR (in %) | |
| Selection order | Wavelength | Calibration | Cross-validation | Selection order | Wavelength | Calibration | Cross-validation | Selection order | Wavelength | Calibration | Cross-validation |
| 1 | 613.58 | 80.5% | 80.4% | 1 | 634.45 | 78.3% | 78.3% | 1 | 613.58 | 95.1% | 95.1% |
| 2 | 484.16 | 89.0% | 89.0% | 2 | 598.97 | 85.7% | 85.6% | 2 | 651.15 | 95.5% | 95.5% |
| 3 | 634.45 | 93.6% | 93.6% | 3 | 665.76 | 87.9% | 87.7% | 3 | 425.71 | 95.8% | 95.7% |
| 4 | 605.23 | 95.1% | 95.1% | 4 | 630.28 | 89.0% | 88.9% | 4 | 617.75 | 95.9% | 95.9% |
| 5 | 588.53 | 95.9% | 95.8% | 5 | 864.07 | 89.8% | 89.7% | 5 | 394.40 | 96.0% | 95.9% |
| 6 | 640.71 | 96.4% | 96.3% | 6 | 548.87 | 90.3% | 90.1% | 6 | 653.24 | 96.1% | 96.0% |
| 7 | 607.31 | 96.8% | 96.7% | 7 | 488.33 | 91.4% | 91.2% | 7 | 659.50 | 96.1% | 96.0% |
| 8 | 434.06 | 97.1% | 97.1% | 8 | 628.19 | 91.7% | 91.6% | 8 | 411.10 | 96.1% | 96.1% |
| 9 | 603.14 | 97.3% | 97.2% | 9 | 661.59 | 92.1% | 92.0% | 9 | 649.06 | 96.2% | 96.2% |
| 10 | 615.66 | 97.4% | 97.4% | 10 | 584.35 | 92.4% | 92.3% | 10 | 404.84 | 96.3% | 96.2% |
| 11 | 630.28 | 97.7% | 97.7% | 11 | 530.08 | 92.7% | 92.6% | 11 | 655.33 | 96.2% | 96.2% |
| 12 | 657.41 | 97.8% | 97.7% | 12 | 636.54 | 92.9% | 92.8% | 12 | 609.40 | 96.3% | 96.2% |
| 13 | 651.15 | 98.0% | 98.0% | 13 | 603.14 | 93.2% | 93.0% | 13 | 586.44 | 96.3% | 96.3% |
| 14 | 601.05 | 98.1% | 98.1% | 14 | 486.25 | 93.4% | 93.3% | 14 | 594.79 | 96.3% | 96.3% |
| 15 | 642.80 | 98.2% | 98.2% | 15 | 546.78 | 93.6% | 93.5% | 15 | 684.55 | 96.4% | 96.3% |
| 16 | 431.97 | 98.3% | 98.3% | 16 | 861.98 | 93.9% | 93.7% | 16 | 553.04 | 96.4% | 96.3% |
| 17 | 488.33 | 98.3% | 98.3% | 17 | 694.99 | 94.0% | 93.8% | 17 | 578.09 | 96.5% | 96.5% |
| 18 | 638.63 | 98.4% | 98.4% | 18 | 429.89 | 94.1% | 94.0% | 18 | 657.41 | 96.5% | 96.5% |
| 19 | 649.06 | 98.4% | 98.4% | 19 | 632.36 | 94.3% | 94.1% | 19 | 636.54 | 96.6% | 96.6% |
| 20 | 598.97 | 98.5% | 98.5% | 20 | 891.20 | 94.4% | 94.3% | 20 | 550.96 | 96.6% | 96.6% |
| 21 | 866.15 | 98.6% | 98.5% | 21 | 582.27 | 94.5% | 94.4% | 21 | 841.10 | 96.7% | 96.6% |
| 22 | 632.36 | 98.6% | 98.6% | 22 | 596.88 | 94.7% | 94.6% | 22 | 615.66 | 96.7% | 96.6% |
| 23 | 592.70 | 98.7% | 98.7% | 23 | 494.60 | 94.8% | 94.7% | 23 | 576.00 | 96.7% | 96.6% |
| 24 | 429.89 | 98.7% | 98.7% | 24 | 532.17 | 94.8% | 94.7% | 24 | 584.35 | 96.8% | 96.7% |

Table 3

Figure 21

Table 8

Branch 1: "GP" versus "GNF+GNN+Y"

| Selection order | Wavelength | Calibration | Cross-validation |
|---|---|---|---|
| 1 | 482.07 | 65.8% | 65.5% |
| 2 | 429.89 | 72.1% | 71.9% |
| 3 | 431.97 | 74.8% | 74.7% |
| 4 | 557.22 | 76.5% | 76.2% |
| 5 | 859.89 | 83.4% | 83.3% |
| 6 | 709.60 | 84.3% | 84.3% |
| 7 | 479.98 | 85.1% | 85.0% |
| 8 | 434.06 | 85.7% | 85.7% |
| 9 | 394.40 | 86.3% | 86.1% |
| 10 | 878.68 | 86.7% | 86.7% |
| 11 | 427.80 | 87.2% | 87.1% |
| 12 | 559.30 | 87.6% | 87.6% |
| 13 | 488.33 | 88.1% | 88.1% |
| 14 | 436.15 | 88.4% | 88.4% |
| 15 | 876.59 | 88.8% | 88.7% |
| 16 | 484.16 | 88.9% | 88.9% |
| 17 | 402.75 | 89.2% | 89.1% |
| 18 | 425.71 | 89.3% | 89.3% |
| 19 | 880.76 | 89.4% | 89.4% |
| 20 | 423.62 | 89.6% | 89.5% |
| 21 | 396.49 | 89.8% | 89.7% |
| 22 | 486.25 | 89.9% | 89.8% |
| 23 | 893.29 | 90.0% | 89.9% |
| 24 | 870.33 | 90.1% | 90.0% |

Branch 2: "Y" versus "GNN+GNF"

| Selection order | Wavelength | Calibration | Cross-validation |
|---|---|---|---|
| 1 | 431.97 | 86.4% | 86.4% |
| 2 | 429.89 | 87.0% | 87.0% |
| 3 | 866.15 | 88.9% | 88.1% |
| 4 | 559.30 | 90.4% | 89.8% |
| 5 | 868.24 | 90.7% | 90.3% |
| 6 | 542.61 | 91.1% | 90.7% |
| 7 | 557.22 | 91.4% | 91.0% |
| 8 | 434.06 | 91.6% | 91.3% |
| 9 | 509.21 | 91.8% | 91.6% |
| 10 | 413.19 | 92.0% | 91.8% |
| 11 | 427.80 | 92.1% | 92.0% |
| 12 | 561.39 | 92.2% | 92.1% |
| 13 | 409.01 | 92.4% | 92.2% |
| 14 | 400.66 | 92.6% | 92.4% |
| 15 | 544.69 | 92.7% | 92.5% |
| 16 | 893.29 | 92.8% | 92.6% |
| 17 | 734.65 | 93.1% | 92.7% |
| 18 | 657.41 | 93.4% | 93.1% |
| 19 | 436.15 | 93.5% | 93.3% |
| 20 | 889.11 | 93.7% | 93.4% |
| 21 | 743.00 | 93.8% | 93.5% |
| 22 | 820.23 | 93.8% | 93.6% |
| 23 | 732.56 | 94.0% | 92.7% |
| 24 | 659.50 | 94.1% | 93.8% |

Branch 3: "GNF" versus "GNN"

| Selection order | Wavelength | Calibration | Cross-validation |
|---|---|---|---|
| 1 | 398.57 | 58.5% | 58.3% |
| 2 | 396.49 | 60.4% | 60.6% |
| 3 | 400.66 | 61.9% | 61.8% |
| 4 | 394.40 | 62.7% | 62.6% |
| 5 | 434.60 | 63.0% | 63.0% |
| 6 | 550.96 | 68.5% | 67.1% |
| 7 | 494.60 | 73.9% | 72.3% |
| 8 | 822.32 | 75.3% | 73.5% |
| 9 | 500.86 | 76.0% | 74.2% |
| 10 | 425.71 | 77.0% | 74.9% |
| 11 | 546.78 | 77.8% | 75.6% |
| 12 | 726.30 | 77.9% | 75.9% |
| 13 | 655.33 | 78.6% | 76.6% |
| 14 | 626.10 | 78.8% | 77.2% |
| 15 | 826.49 | 79.1% | 77.4% |
| 16 | 505.03 | 79.5% | 77.8% |
| 17 | 874.50 | 79.5% | 78.0% |
| 18 | 634.45 | 79.7% | 78.0% |
| 19 | 657.41 | 79.8% | 78.4% |
| 20 | 649.06 | 79.9% | 78.5% |
| 21 | 818.14 | 80.2% | 78.7% |
| 22 | 847.37 | 80.2% | 78.9% |
| 23 | 667.85 | 80.3% | 79.0% |
| 24 | 786.83 | 80.2% | 79.1% |

Figure 22

Table 10

1st Branch: "Y" versus "GNF+GNN+GP"

| Selection order | Wavelength | BCR (in %) Calibration | BCR (in %) Cross-validation |
|---|---|---|---|
| 1 | 475.81 | 84.3% | 84.3% |
| 2 | 540.52 | 84.8% | 84.7% |
| 3 | 717.95 | 85.7% | 85.9% |
| 4 | 486.25 | 85.8% | 86.1% |
| 5 | 657.41 | 86.2% | 86.3% |
| 6 | 701.25 | 86.3% | 86.6% |
| 7 | 845.28 | 86.7% | 86.8% |
| 8 | 680.37 | 86.8% | 86.9% |
| 9 | 490.42 | 86.9% | 87.0% |
| 10 | 655.33 | 87.1% | 87.2% |
| 11 | 684.55 | 87.2% | 87.4% |
| 12 | 686.64 | 87.3% | 87.4% |
| 13 | 659.50 | 87.5% | 87.5% |
| 14 | 803.53 | 87.6% | 87.7% |
| 15 | 728.38 | 87.6% | 87.7% |
| 16 | 682.46 | 87.7% | 87.8% |
| 17 | 582.27 | 87.7% | 87.9% |
| 18 | 546.78 | 87.8% | 87.9% |
| 19 | 651.15 | 87.8% | 88.0% |
| 20 | 661.59 | 88.0% | 88.1% |
| 21 | 571.83 | 88.0% | 88.1% |
| 22 | 454.93 | 88.0% | 88.1% |
| 23 | 617.75 | 88.0% | 88.1% |
| 24 | 400.66 | 88.0% | 88.2% |

2nd Branch: "GP" versus "GNN+GNF"

| Selection order | Wavelength | BCR (in %) Calibration | BCR (in %) Cross-validation |
|---|---|---|---|
| 1 | 431.97 | 75.5% | 75.6% |
| 2 | 427.80 | 77.2% | 77.2% |
| 3 | 477.90 | 80.3% | 80.3% |
| 4 | 434.06 | 81.8% | 81.8% |
| 5 | 891.20 | 83.3% | 83.2% |
| 6 | 559.30 | 87.5% | 87.4% |
| 7 | 872.41 | 88.2% | 88.2% |
| 8 | 486.25 | 88.8% | 88.7% |
| 9 | 394.40 | 89.2% | 89.2% |
| 10 | 429.89 | 89.8% | 89.7% |
| 11 | 398.57 | 90.1% | 90.1% |
| 12 | 438.24 | 90.3% | 90.3% |
| 13 | 880.76 | 90.5% | 90.5% |
| 14 | 465.37 | 90.7% | 90.7% |
| 15 | 396.49 | 90.9% | 90.9% |
| 16 | 517.56 | 91.1% | 91.0% |
| 17 | 557.22 | 91.3% | 91.3% |
| 18 | 406.92 | 91.5% | 91.5% |
| 19 | 421.54 | 91.6% | 91.6% |
| 20 | 436.15 | 91.8% | 91.7% |
| 21 | 511.29 | 91.9% | 91.9% |
| 22 | 882.85 | 92.1% | 92.0% |
| 23 | 425.71 | 92.1% | 92.1% |
| 24 | 423.62 | 92.3% | 92.3% |

3rd Branch: "GNF" versus "GNN"

| Selection order | Wavelength | BCR (in %) Calibration | BCR (in %) Cross-validation |
|---|---|---|---|
| 1 | 398.57 | 58.5% | 58.3% |
| 2 | 396.49 | 60.4% | 60.6% |
| 3 | 400.66 | 61.9% | 61.8% |
| 4 | 394.40 | 62.7% | 62.6% |
| 5 | 434.06 | 63.0% | 63.0% |
| 6 | 550.96 | 68.5% | 67.1% |
| 7 | 494.60 | 73.9% | 72.3% |
| 8 | 822.32 | 75.3% | 73.5% |
| 9 | 500.86 | 76.0% | 74.2% |
| 10 | 425.71 | 77.0% | 74.9% |
| 11 | 546.78 | 77.8% | 75.6% |
| 12 | 726.30 | 77.9% | 75.9% |
| 13 | 655.33 | 78.6% | 76.6% |
| 14 | 626.10 | 78.8% | 77.2% |
| 15 | 826.49 | 79.1% | 77.4% |
| 16 | 505.03 | 79.5% | 77.8% |
| 17 | 874.50 | 79.5% | 78.0% |
| 18 | 634.45 | 79.7% | 78.0% |
| 19 | 657.41 | 79.8% | 78.4% |
| 20 | 649.06 | 79.9% | 78.5% |
| 21 | 818.14 | 80.2% | 78.7% |
| 22 | 847.37 | 80.2% | 78.9% |
| 23 | 667.85 | 80.3% | 79.0% |
| 24 | 786.83 | 80.2% | 79.1% |

Figure 23

METHOD FOR IDENTIFYING YEAST OR BACTERIA FROM A LUMINOUS INTENSITY REFLECTED BY, OR TRANSMITTED THROUGH, AN ILLUMINATED MICROORGANISM

FIELD OF THE INVENTION

The invention relates to the field of microbiological analysis, and in particular the characterization of microorganisms, notably the identification of yeasts and bacteria, and in the context of the latter, identification of their Gram type and of their fermenting or nonfermenting character.

Advantageously, the invention applies to the analysis of a hyperspectral or multispectral image of a bacterial colony or of yeast that has grown in a nonchromogenic, nonfluorogenic, dye-free culture medium.

PRIOR ART

In the field of pathogenic microorganisms, characterization of a microorganism preferably consists of identifying its species and its sensitivity to an antimicrobial agent (or "antibiogram"), in order to determine a treatment for a patient infected with this microorganism. For this purpose, a complex microbiological process is usually employed in the laboratory, said process most often requiring prior knowledge of other properties of the microorganism, notably its kingdom (e.g. yeast or bacterium), and in the bacterial context its Gram type or its fermenting or nonfermenting character. In fact, this information notably makes it possible to select a culture medium or a type of antimicrobial agents suitable for the microorganism in order to determine, finally, its species or its antibiogram. For example, the choice of a gallery for identification of microorganisms API® marketed by the applicant is based on knowledge of the microorganism's kingdom (e.g. yeast vs bacterium) or Gram type of the bacterial strain to be identified. Similarly, determination of the antibiogram of a bacterial strain by the Vitek® 2 system marketed by the applicant is based on the choice of a card depending on the Gram type and fermenting or nonfermenting character of said strain. We may also mention identification by MALDI-TOF mass spectrometry using a different matrix depending on whether the microorganism to be identified is a yeast or a bacterium. Thus, knowing this information as early as possible makes it possible to optimize the microbiological process, notably by accelerating the latter or reducing the number of consumables used.

Knowledge of these properties also makes it possible to reduce false positives in the identification of bacterial strains. As an example, in the context of the ChromID® Elite medium marketed by the applicant, knowledge of the fermenting character of the bacterial strain tested strengthens the identification of the salmonellae. In particular, a salmonella, a fermenting bacterium, and a *Pseudomonas*, a nonfermenting bacterium, both cause a change of the chromogenic substrate. If it is known that the bacterium is nonfermenting, salmonella can simply be rejected without an additional microbiological assay.

Besides characterization of a microorganism with a view to guiding the microbiological process in the laboratory, this information is also clinically useful. Notably, the Gram classification of a bacterial strain makes it possible to characterize the wall of the latter, for example its percentage of peptidoglycan, and is used in bacterial taxonomy or for evaluating the sensitivity of bacteria to antibiotics, to a first approximation. Thus, a distinction is made between two types of bacteria, namely the Gram "positive" bacteria and the Gram "negative" bacteria. It is also observed that the nonfermenting bacteria, i.e. the bacteria unable to catabolize glucose, occupy a special place among the pathogenic bacteria. In fact, they have a high level of natural resistance to antibiotics and are implicated in many nosocomial infections. As examples, we may mention *Pseudomonas aeruginosa* and *Acinetobacter*. Quickly establishing the fermenting or nonfermenting character of a bacterium thus allows the first-line antibiotic therapy to be directed more effectively, slowing the spread of multi-resistant strains.

Historically, each of the properties mentioned above (kingdom, Gram and fermenting) has been obtained by a dedicated technique. For example, the Gram type of a bacterial strain was determined by a manual technique called "Gram staining", which comprises a large number of manual steps (fixation, staining, mordanting, washing, overstaining, etc.), and therefore takes a long time. Various techniques have therefore been developed for automating detection of the Gram type of the bacteria, notably in order to treat a large number of samples. However, these techniques essentially continue to alter the electromagnetic response of the bacteria or of their environment to make their Gram easily observable. In particular, a first type of technique consists of automating the staining of the bacterial membrane on microscope slides, but the step for a final decision about the Gram type is always carried out by a technician who observes the slides under the microscope. Therefore techniques of this type are not fully automated, and moreover are difficult to automate. In fact, the color difference between the Gram positive bacteria and the Gram negative bacteria may be subtle, which explains why the intervention of a laboratory technician is still necessary. A second type of technique consists of bringing the bacteria into contact with a substrate that is degraded by an enzymatic reaction initiated by the peptidoglycans of the membranes of the bacteria. This reaction produces chromophores or fluorophores, whose concentration is an indication of the Gram. It is usually called chromogenic or fluorogenic "labeling" of the bacteria. Although techniques of this type from the prior art can be automated, for example by measuring the luminous intensity of the chromophores/fluorophores using a suitable device (e.g. spectrometer/fluorometer) and then comparing, by computer, the measured intensity against predefined threshold values, they nevertheless require the design of special chromophore or fluorogenic substrates, which are often expensive. Furthermore, whatever technique is used, the bacteria are altered from their natural state (e.g. they comprise dyes, are labeled with chromogenic or fluorescent markers, etc.), and therefore are no longer usable for subsequent tests for characterization (e.g. determination of an antibiogram).

Regarding determination of the fermenting or nonfermenting character of a bacterium, it usually employs chromogenic media that change color depending on the fermenting or nonfermenting character of the bacterial strain tested. For example, the "Kligler-Hajna" assay consists of growing the strain on a culture medium comprising a colorimetric indicator that changes color as a function of pH, lactose, glucose, thiosulfate, and ferrous ions. This medium detects the fermenting character of the bacterium from the catabolization of glucose, which is reflected in a colorimetric color change of the pH indicator. We may also mention the assay media for the tributyrin esterase activity of the bacterial strain, which allow characterization of the nonfermenting Gram-negative bacteria.

SUMMARY OF THE INVENTION

The aim of the present invention is to propose a method for characterizing a microorganism that is automatic and does not require the microorganism or its culture medium to be labeled or stained to determine these characteristics.

For this purpose, the invention relates to a method for characterizing a microorganism, comprising:
- illuminating, in the wavelength range 390 nm-900 nm, the microorganism having a natural electromagnetic response in said range;
- acquiring, in said range, a luminous intensity reflected by, or transmitted through, said illuminated microorganism; and
- determining the microorganism as being a yeast or a bacterial strain, depending on the luminous intensity acquired in said range.

"Natural electromagnetic response" means, in the sense of the invention, that the microorganism, a yeast or a bacterial strain, is not altered by elements (dye, chromogen, fluorogen, etc.) that alter its electromagnetic response to illumination at least in the wavelength range of interest. For example, a colony of the microorganism is cultured in a nonchromogenic and nonfluorescent culture medium and the illumination/acquisition is effected directly on the colony still present in its medium.

In other words, the inventors discovered that in the wavelength range 390 nm-900 nm the yeasts and the bacteria "naturally" have an electromagnetic signature allowing them to be differentiated. Thus, it is not necessary to use a chromogenic or fluorogenic substrate or dyes. Moreover, the method according to the invention is quick insofar as it consists of illuminating, measuring a spectrum and carrying out processing, notably computer processing, of this spectrum. This characterization of the microorganism at the yeast or bacterium level makes it possible for example to optimize a laboratory microbiological process as described above.

Note that characterization of the microorganism as being a yeast or a bacterium is performed directly from the acquired luminous intensity, without requiring prior determination of the species of the microorganism. Notably, not having to identify at the species level offers the advantage of greatly simplifying the prediction model, since the latter can be limited to two classes.

Advantageously, the method is applied to a Petri dish comprising a nutrient agar medium, on which colonies of microorganisms have grown. For example, the nutrient medium is seeded using a biological sample containing, or suspected of containing, yeasts or bacteria, e.g. urine, and then cultured to grow the colonies. As soon as a colony is detected on the culture medium, it is characterized by the method of the invention. Thus, the method does not require any transfer of material or addition of reagent following seeding of the culture medium. For example, a colony is detected automatically by taking images of the Petri dish at regular intervals and employing a colony detecting algorithm.

Advantageously, the method according to the invention is not based on analysis of the autofluorescence of the microorganism but on analysis of its reflectance or its absorbance. In particular, the illumination is generally too intense for the autofluorescence to be observable on a hyperspectral or multispectral image.

According to one embodiment, the method further comprises detection of the Gram type and of the fermenting character of a bacterial strain, comprising:
- illuminating, in the wavelength range 390 nm-900 nm, at least one bacterium of said strain having a natural electromagnetic response in said range;
- acquiring, in said range, a luminous intensity reflected by, or transmitted through, said illuminated bacterium; and
- determining the Gram type and the fermenting character of the bacterial strain depending on the luminous intensity acquired in said range.

In other words, bacteria "naturally" have an electromagnetic signature characteristic of their Gram type and of their fermenting or nonfermenting character. The method according to the invention thus consists of measuring this signature and then extracting therefrom the Gram type and the fermenting character of the bacterium. In particular, thanks to the invention it is possible to determine thanks to the range 390-900 nm whether the bacterial strain is Gram positive or Gram negative and fermenting or Gram negative and nonfermenting, knowledge of this information making it possible for example to optimize a laboratory microbiological process as described above.

The invention also relates to a method for calibrating a system for implementing a method according to the invention, the system comprising:
- illumination configured for illuminating, in the wavelength range 390 nm-900 nm, a microorganism;
- a sensor configured for acquiring, in the range 390 nm-900 nm, a luminous intensity reflected by, or transmitted through, said illuminated microorganism; and
- a computer unit comprising a computer memory able to contain instructions for analyzing the intensity acquired by the sensor and a microprocessor able to execute the analysis instructions contained in the computer memory, the method of calibration comprising the steps of:
- constructing a learning database comprising luminous intensities in the range 390 nm-900 nm of bacteria and of yeasts illuminated in said range;
- implementing, by computer, automated learning of a prediction model of yeast or of bacteria as a function of said database; and
- storing, in the system's computer memory, analysis instructions for implementing the prediction model learnt.

The invention also relates to a therapeutic method comprising:
- taking a sample from a patient suspected of having an infection with a yeast or a bacterium;
- detecting one or more microorganisms present in the sample, advantageously by seeding an agar culture medium with the sample, culturing said seeded medium to grow colonies of microorganisms and detecting one or more colonies that have grown;
- determining the microorganism as being a yeast or a bacterial strain, depending on the luminous intensity acquired in said range;
- selecting one or more antimicrobials as a function of the result of said determination; and
- administering the selected antimicrobial or antimicrobials to the patient.

BRIEF DESCRIPTION OF THE FIGURES

The invention will be better understood on reading the following description, given purely as an example, and referring to the appended drawings, in which identical references denote identical or similar elements, and in which

FIG. 3 is an example of a transmission spectrum of a bandpass filter used in the system in

FIG. 2;

FIG. 8 is a table describing the bacterial species and yeast species used for prediction model learning of the classes Y, GP, GNF, GNN;

FIGS. 9 and 10 are tables, respectively for the COS medium and the TSA medium, describing the number of pixels, and therefore of spectra, used for calibration and cross validation of the prediction models;

FIG. 11 is a diagram illustrating the calculation of a weighted prediction rate, or "balanced classification rate"

FIG. 21 summarizes BCRs and relationships for solving an optimization problem in models of FIG. 7C and obtained using the step-forward approach in FIG. 4;

FIG. 22 summarizes BCRs and relationships for solving an optimization problem in models of FIG. 7C and obtained using the step-forward approach in FIG. 5;

FIG. 23 summarizes BCRs and relationships for solving an optimization problem in models of FIG. 7B and obtained using the step-forward approach in FIG. 4.

DETAILED DESCRIPTION OF THE INVENTION

Hereinafter, the notation $A_{i,j}$ relates to the element of the i-th row and j-th column of the matrix A.

Figure 1:
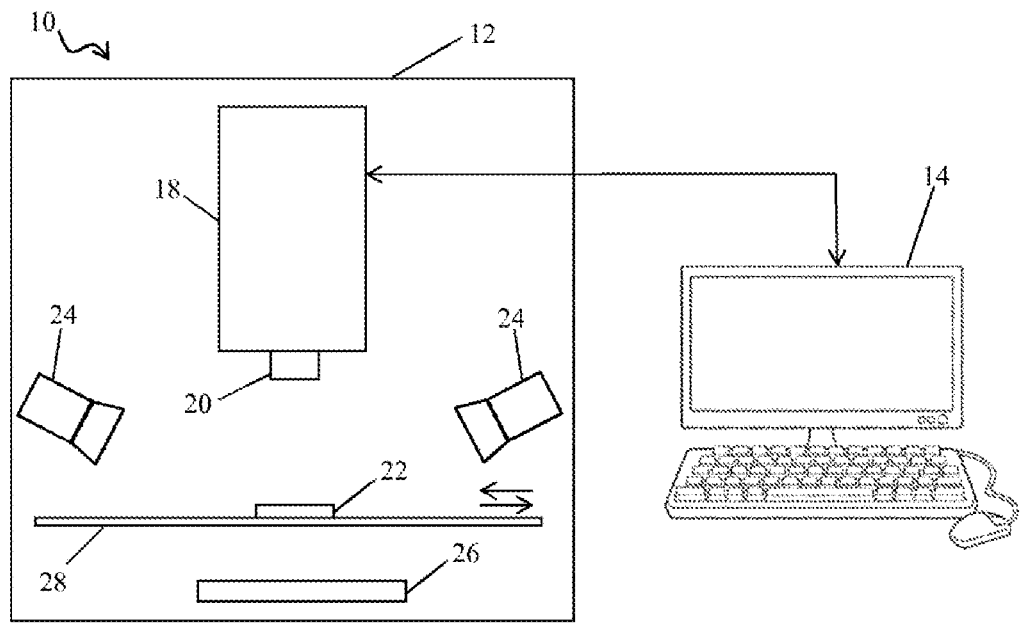
FIG. 1 is a schematic view of a hyperspectral system according to the invention.

Referring to FIG. 1, a hyperspectral system 10 for characterization of colonies of yeasts or of bacteria that have grown on agar poured in a Petri dish comprises:

a device 12 for hyperspectral image acquisition; and a computer data processing unit 14 connected (e.g. by a link or wireless wired) to the device 12 for controlling it and for receiving and processing the images acquired by the device 12.

The device 12, for example a hyperspectral imaging system of reference "Pika 11" from the company Resonon, Montana USA, comprises:

a so-called "hyperspectral" camera 18, consisting of a digital sensor comprising an array of elementary sensors, for example a digital sensor of the CCD or CMOS type, sensitive in the wavelength range $[\lambda_{min}; \lambda_{max}] = [390; 900]$ nanometers, and a light scattering element or a spectrograph for selecting a wavelength to be acquired by the sensor;

an objective 20 for focusing, on the digital sensor of the camera 18, the optical image of a Petri dish 22, of which a hyperspectral image is to be acquired;

front illumination 24, for example consisting of one or more halogen lamps, e.g. 2 or 4 lamps, able to emit light in the range $[\lambda_{min}; \lambda_{max}]$ and for providing uniform front illumination of the Petri dish 22. For example, the illumination comprises lamps with white light;

rear illumination 26, for example consisting of a matrix of white-light LEDs, for providing uniform rear illumination of the Petri dish 22 in the range $[\lambda_{min}; \lambda_{max}]$; and a carriage 28 carrying Petri dish 22 and allowing the latter to pass in front of the objective 20 in order to obtain a complete image of the dish 22 by scanning.

Illumination is thus provided in the whole range $[\lambda_{min}; \lambda_{max}]$.

The device 12 is for example configured for acquiring the image of a region of 90 millimeters by 90 millimeters with a sampling step of 160 micrometers (spatial resolution estimated at 300 micrometers) and with a spectral resolution of 1.7 nanometer over the range $[\lambda_{min}; \lambda_{max}]$ The device 12 thus produces a digital image HSI of the light reflected by the Petri dish, having N rows and M columns, the Petri dish 22 preferably being open (i.e. without its cover):

$$HSI(\lambda) = \begin{pmatrix} Rad_{1,1}(\lambda) & \ldots & Rad_{1,j}(\lambda) & \ldots & Rad_{1,M}(\lambda) \\ \vdots & \ddots & \vdots & & \vdots \\ Rad_{i,1}(\lambda) & \ldots & Rad_{i,j}(\lambda) & \ldots & Rad_{i,M}(\lambda) \\ \vdots & & \vdots & \ddots & \vdots \\ Rad_{N,1}(\lambda) & \ldots & Rad_{N,j}(\lambda) & \ldots & Rad_{N,M}(\lambda) \end{pmatrix} \quad (1)$$

The radiance of a pixel, commonly called "luminous intensity", in this case corresponds to the amount of light incident on the surface of the corresponding elementary sensitive site of the camera's sensor 18 during the exposure time, as is known per se from the field of digital photography for example.

Each pixel $Rad_{i,j}(\lambda)$ consists of a digital spectrum of the radiance of the dish 22 corresponding to the pixel at different wavelengths $[\lambda_{min}; \lambda_{max}]$, the digital spectrum being expressed by the relation:

$$\forall\,(i,j)\in[1,N]\times[1,M]\colon Rad_{i,j}(\lambda)=\begin{pmatrix}Rad_{i,j}(\lambda_{min})\\ Rad_{i,j}(\lambda_{min}+\Delta\lambda)\\ Rad_{i,j}(\lambda_{min}+2\times\Delta\lambda)\\ \vdots\\ Rad_{i,j}(\lambda_{min}+p\times\Delta\lambda)\\ \vdots\\ Rad_{i,j}(\lambda_{max})\end{pmatrix} \quad (2)$$

where $\Delta\lambda$ is the spectral resolution and p is a positive integer belonging to $$\left[0, P = \frac{\lambda_{max} - \lambda_{min}}{\Delta\lambda}\right].$$

The acquisition wavelengths $\lambda_{min}+P\times\Delta\lambda$ are usually denoted by the term "channels".

The data processing unit 14 is for example a personal computer, a tablet, a smart phone, a server, a supercomputer, or more generally any system based on microprocessor(s), notably of the DSP ("digital signal processor") type, based on circuits of the FPGA type, based on circuits mixing these types of technology, etc., configured for processing the images HSI produced by the acquisition device 12. The unit 14 is notably provided with the set of memories (RAM, ROM, cache, bulk storage, etc.) for storing the images produced by the device 12, computer instructions for execution of the method according to the invention, parameters useful for said execution and for storing the results of the intermediate and final calculations. The unit 14 optionally comprises a display screen for displaying the final result of the characterization of the colonies, in particular determination of the Gram type and/or fermenting character, and/or of the bacterial or yeast character of the colonies investigated. Although a single processing unit is described, the invention applies of course to processing carried out by several processing units (e.g. a unit mounted inside the camera 18 for carrying out preprocessing of images HSI and a unit outside the device 12 for carrying out the rest of the processing). Moreover, the system may be supplemented with an interface allowing input of data relating to the sample into the unit 14, notably the type of culture medium used when the prediction depends on the medium, for example by means of a keyboard/mouse and a drop-down menu available to the operator, a barcode/QR code reader, reading a barcode/QR code present on the Petri dish and comprising information about the medium, etc.

The hyperspectral system in FIG. 1 has the advantage of being nimble in terms of acquisition wavelengths as it is able to adapt to different models for predicting the class of the colonies and can use a large number of spectral channels to increase the prediction accuracy. In addition to a high price, such a system generally has a lower spatial resolution than a conventional CMOS or CCD camera, whose aim is solely to acquire an image in intensity of the light incident on its sensor.

Figure 2:
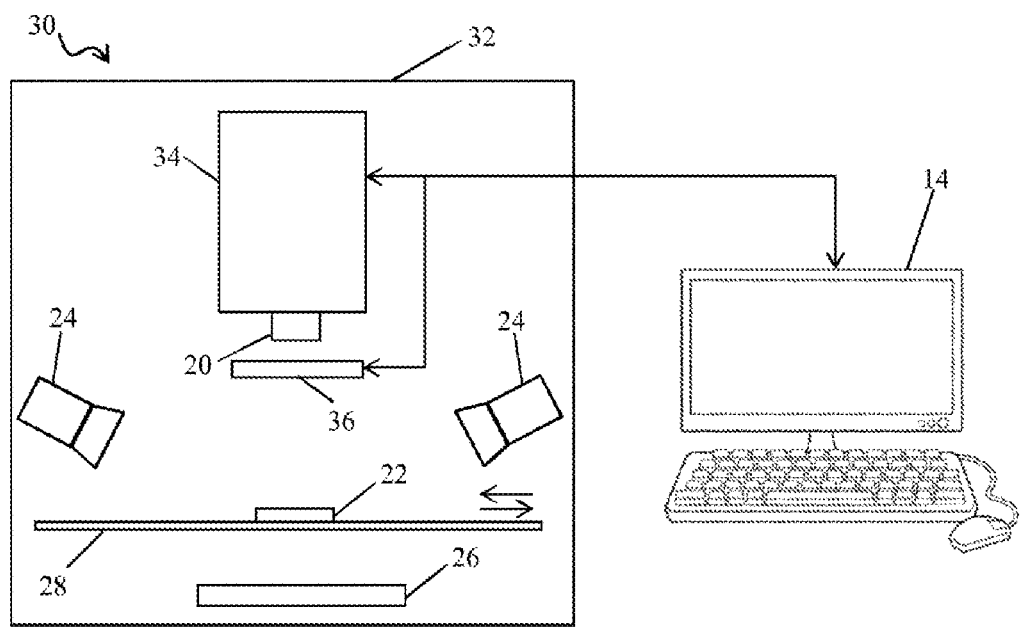
FIG. 2 is a schematic view of a multispectral system according to the invention.
Figure 3:
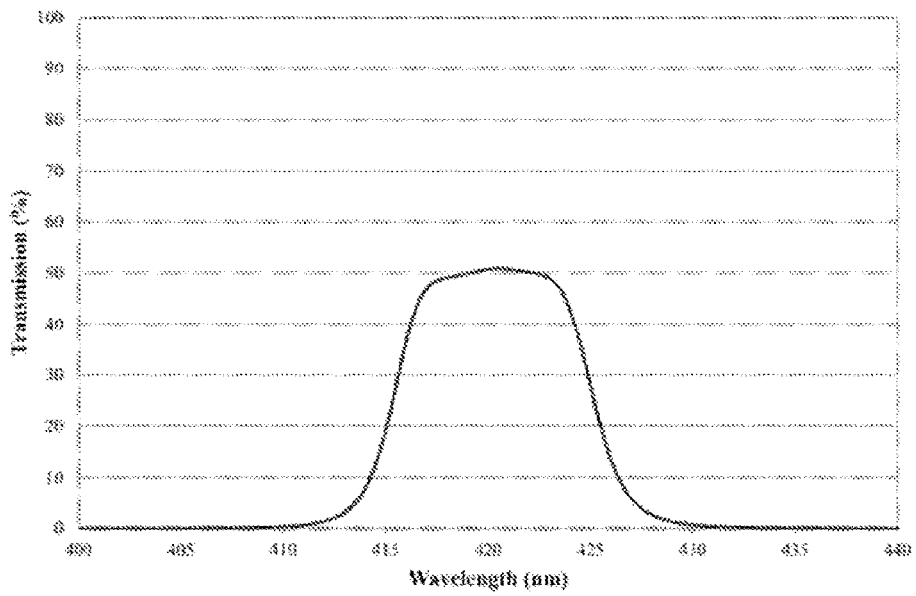

Referring to FIG. 2, a multispectral system 32 differs from the hyperspectral system 10 by the camera 32, advantageously a CMOS or CCD camera with high spatial resolution, coupled to a set of spectral filters 36, for example arranged in front of the objective 20 between the objective 20 and the camera's sensor 32. The set of filters 36 consists of a number $N_F$ of separate bandpass filters, each configured for transmitting only the light in a range [$\lambda_1$; $\lambda_2$] of the range [$\lambda_{min}$; $\lambda_{max}$], with a spectral full width half maximum (FWHM) less than or equal to 50 nm, and preferably less than or equal to 20 nm. The transmission spectrum of a filter of this kind, e.g. a filter from the company Edmund Optics centered on 420 nm, is illustrated in FIG. 3. The set 36 is for example a filter wheel that can receive up to 24 different filters, the wheel being controlled by the unit 14, which actuates it to cause said filters to pass along in front of the camera and control the taking of an image for each of them.

A multispectral image HSI($\lambda$) is thus acquired, each pixel of which $Rad_{i,j}(\lambda)$ consists of a digital spectrum of the radiance of the dish 22 corresponding to the pixel at the different spectral bands filtered by the set 36, the digital spectrum being expressed by the relation:

$$\forall\,(i,j)\in[1,N]\times[1,M]\colon Rad_{i,j}(\lambda)=\begin{pmatrix}Rad_{i,j}(\lambda_1)\\ Rad_{i,j}(\lambda_2)\\ \vdots\\ Rad_{i,j}(\lambda_{N_F})\end{pmatrix} \quad (3)$$

where $\lambda_1, \lambda_2, \ldots, \lambda_{N_F}$ are respectively the central wavelengths of the spectral filters of the set 36.

Figure 4:
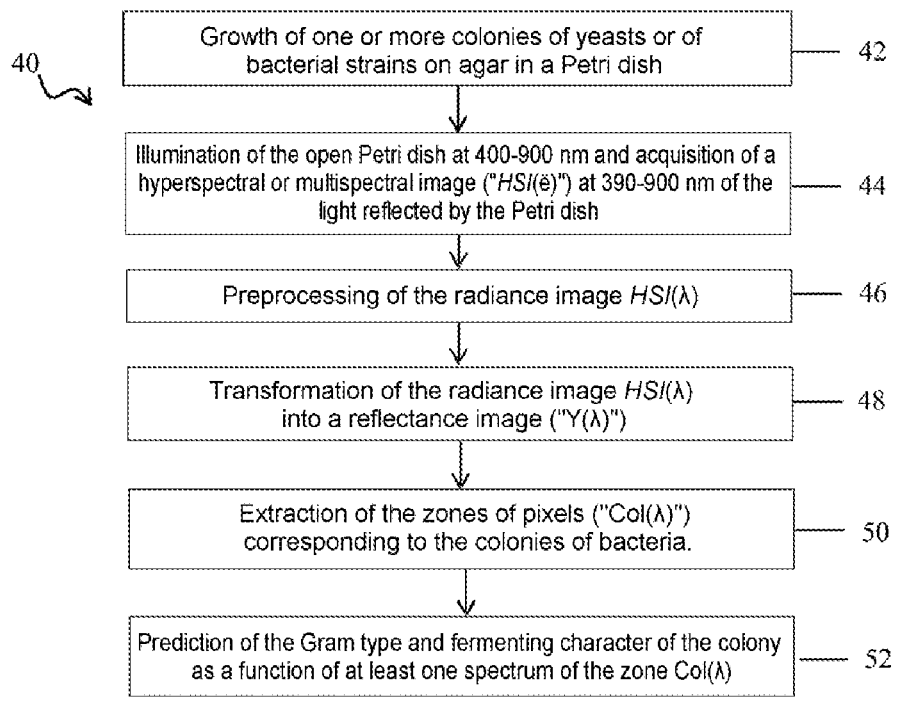
FIG. 4 is a flowchart of a method for predicting the classes Y, GP, GNF, GNN applied using the system in FIG. 1 or FIG. 2.

A method 40 for characterization of microorganisms contained in a biological sample (e.g. urine, blood, bronchoalveolar sample, etc.) by means of the system that has just been described is now presented in detail in connection with the flowchart in FIG. 4. In particular, this method advantageously finds application in the context of a more general method for identifying the microorganisms contained in said sample using MALDI-TOF mass spectrometry (e.g. Vitek® MS marketed by the applicant) and an antibiogram of said microorganisms (e.g. using the Vitek® 2 platform marketed by the applicant). As is known per se, each of these techniques requires selecting media and/or reagents and/or particular consumables in relation to the type of microorganism. As an example, identification of yeasts by MALDI-TOF mass spectrometry advantageously involves the use of formic acid in the matrix used in this type of technology. Moreover, the choice of the card of the Vitek® 2 platform (card comprising a growth medium and one or more antimicrobials tested in the antibiogram) depends on the bacterial character of the microorganism tested. Notably, the fermenting, Gram-negative bacteria require a particular card for generating their antibiogram.

Advantageously, the method of characterization 40 described hereunder makes it possible, starting from the first growth on the Petri dish, to obtain the necessary information about the microorganisms for the rest of the microbiological process, in particular to know whether a colony that has grown corresponds to a yeast ("Y") or a bacterium, and in the case of a bacterium, whether this bacterium is of the Gram-positive type ("GP") or Gram-negative type ("GN"), and in the context of a bacterium of the Gram-negative type, whether this bacterium is fermenting ("GNF") or nonfermenting ("GNN"). The method thus makes it possible to predict the class of a microorganism, namely the class Y, GP, GNF or GNN.

In a first step 42 of the method, a Petri dish is seeded with a biological sample, e.g. taken from a patient, so as to grow colonies of yeasts or bacteria on the surface of a nutrient, or "culture" medium, deposited in the Petri dish. The main aim of the culture medium is to grow said colony, and optionally to reinforce the accuracy of the characterization by limiting the light perturbations. Preferably, regarding detection of the Gram type as a function of the reflected luminous intensity, the culture medium is opaque, which increases the level of accuracy of detection. Notably, the opaque medium has a reflectance factor ρ less than or equal to 10%, and preferably less than or equal to 5%, and even more preferably less than or equal to 1%. For example, the so-called "CPSO" agar culture medium ("CPS" agar comprising $SiO_2$ for opacifying the medium), a "columbia" agar (or "CNA" agar), a Columbia agar with 5% of sheep blood (or "COS" agar), a Man, Rogosa, Sharpe agar ("MRSM" agar), a chocolate agar ("PVX" agar), a Tryptone-Soy agar ("TSA" agar), etc.

As this type of growth of colonies is conventional, it will not be described in more detail hereafter. It may advantageously be carried out manually by an operator or automatically using an automatic seeding machine in a manner known per se. Advantageously, preparation is carried out in such a way that the colonies, based on which the characterization of the microorganism is carried out, are spaced apart and in such a way that the area of a colony corresponds to a plurality of pixels in the image acquired by the device 12. This can notably facilitate their subsequent identification in the image acquired, and therefore their segmentation by means of an image processing algorithm or their extraction from the image by a user.

Once growth of the colonies has ended, for example after a time of 24h, 36h or 48h, the Petri dish is preferably opened, arranged on the carriage 28, the illumination 24 and 26 is switched on and at least one hyperspectral (or respectively multispectral) image HSI of the Petri dish is acquired, at 44, using the acquisition device 12 (or respectively 32) and stored in the processing unit 14, which uses computer processing for determining the type of microorganism making up the colony, from the images acquired.

The unit 14 begins optionally, at 46, with preprocessing of the noise, consisting of one of the following processing operations or any combination of these processing operations:
a. correction of the noise of the camera's sensor, notably its offset, its spatial noise, etc., in a manner known per se;
b. processing of the parasitic reflections, notably specular forming "highlights" in the image HSI. For example, thresholding used for removing the pixels that have values above a predetermined threshold, e.g. greater than or equal to two thirds of the maximum value that the pixels can have (i.e. greater than or equal to 170 in the case of 8-bit encoded pixels between 0 and 255);
c. ratiometric processing, making it possible to attenuate the variations in the images caused by external fluctuations such as variations in illumination, by dividing the image HSI by a luminous intensity reflected at a wavelength that is invariant with the type of bacterium and the type of agar used;
d. if several images HSI have been acquired, finding and removing aberrant pixel values and/or the average of the images acquired.

Advantageously, the processing continues, at 48, with transformation of the pre-processed image HSI, which stores values of radiance at different wavelengths, in a hyperspectral or multispectral reflectance image in order to extract the signal generated by the Petri dish alone. This notably makes it possible to filter the fluctuations of the emission spectrum of the sources of illumination 24, 26. For example, a correction of the type "flat field correction" (FFC) is used to obtain the reflectance, which in addition has the advantage of correcting the dispersions of response of the sensor from pixel to pixel (dispersion of the dark current, dispersion of the gain, etc.).

In the context of a hyperspectral image, this transformation is for example a correction according to the relations:

$$\forall (i,j) \in [1,N] \times [1,M], \forall p \in [0,P]: \quad (4)$$

$$Y_{i,j}(\lambda_{min} + p \times \Delta\lambda) = \frac{Rad_{i,j}(\lambda_{min} + p \times \Delta\lambda) - B_{i,j}(\lambda_{min} + p \times \Delta\lambda)}{W_{i,j}(\lambda_{min} + p \times \Delta\lambda) - B_{i,j}(\lambda_{min} + p \times \Delta\lambda)} \times m(\lambda_{min} + p \times \Delta\lambda)$$

where $Y(\lambda)$ is a reflectance image, W is a hyperspectral image stored in the unit 14 of a neutral object of high reflectance illuminated by the illumination 24, 26, for example a sheet with uniform reflectance above 90% (e.g. a so-called "white" sheet or with a gray card less than 10%), and B is a hyperspectral image stored in the unit 14 of a neutral object with low reflectance, for example the image of a black cap covering the objective 20 and $m(\lambda_{min}+p \times \Delta\lambda)=1$ or equal to the average of the matrix $W(\lambda_{min}+p \times \Delta\lambda)-B(\lambda_{min}+p \times \Delta\lambda)$.

Similarly, in the context of a multispectral image, the transformation is for example a correction according to the relation:

$$\forall (i,j) \in [1,N] \times [1,M], \forall n \in [1,N_f]: \quad (5)$$

$$Y_{i,j}(\lambda_n) = \frac{Rad_{i,j}(\lambda_n) - B_{i,j}(\lambda_n)}{W_{i,j}(\lambda_n) - B_{i,j}(\lambda_n)} \times m(\lambda_n)$$

where W is a multispectral image stored in the unit 14 of a neutral object with high reflectance, illuminated by the illumination 24, 26, for example a sheet with uniform reflectance above 90% (e.g. a so-called "white" sheet or with a gray card less than 10%), and B is a multispectral image stored in the unit 14 of a neutral object with low reflectance, for example the image of a black cap covering the objective 20 and $m(\lambda_n)=1$ or equal to the average of the matrix $W(\lambda_n)-B(\lambda_n)$.

The unit 14 carries out, at 50, following step 38 or in parallel with the preceding steps, an algorithm for identifying the colonies of bacteria, e.g. from the image $HSI(\lambda)$ or $Y(\lambda)$. Any conventional shape and object recognition algorithm may be used for extracting a zone of the image, called "$Col(\lambda)$", corresponding to a colony. As a variant, this selection is performed manually by an operator, who selects this zone with the aid of the display screen and a pointing device of the mouse type for example. As an example, the zone $Col(\lambda)$ consists of a list of the coordinates of pixels belonging to the colony. The selected zones of pixels are stored by the unit 14.

The method continues, at 52, with prediction of the class Y, GP, GNF or GNN of the microorganism of the colony as a function of at least one spectrum of the zone $Col(\lambda)$ by applying predefined decision rules, variants of which are described hereunder. In particular, this prediction is carried out as a function of the spectrum $Y_{i,j}(\lambda)$ of each pixel (i, j) of the zone $Col(\lambda)$. For this purpose, a first prediction of the class is carried out for each pixel (i,j) of the zone $Col(\lambda)$, then a majority vote is used for the final prediction of the class. In a first variant, a simple majority vote is used, i.e. the class predicted on the basis of the greatest number of pixels of the zone $Col(\lambda)$ is the class finally retained. In a second variant, in order to increase the certainty in prediction of the class, a qualified vote is used, i.e. the class finally retained is the one that is predicted on the basis of more than X % of the number of pixels making up the zone Col(λ), with X strictly greater than 50%, and preferably greater than or equal to 70%. If no class fulfils this condition, the method then returns an absence of prediction of class. Of course, the class of the colony may be provided by a single value, for example the average spectrum $Y_{col}(\lambda)$ of the set $\{Y_{i,j}(\lambda)\}_{(i,j)\in Col(\lambda)}$ of the spectra of the zone Col(λ).

The class Y, GP, GNF or GNN of each colony is found by the unit 14 by applying predefined prediction rules, variants of which are described hereunder. The classes predicted are stored in the unit 14 and/or displayed on a screen for the user's attention. This prediction is also advantageously sent to another microbial analysis instrument for a subsequent step of identification and/or antibiogram of the microorganisms that formed the colonies.

Various models will now be described for predicting a class Y, GP, GNF or GNN as a function of a spectrum $Y_{i,j}(\lambda)$ of a pixel of a colony, notably prediction models based on supervised automatic learning ("SML": supervised machine learning). The SML tools used are first described with reference to FIG. 5 and then the prediction models are described below through their learning process illustrated in FIGS. 6 and 7.

A. Tools for Supervised Machine Learning

Whatever learning is considered, it begins with the construction of a learning database. For each class Y, GP, GNF and GNN, bacteria and yeasts are selected and each of them is seeded on agar poured in a Petri dish, cultured for a predetermined time, and a hyperspectral image of the dish is acquired with the system described in FIG. 1, and consequently under the same conditions of illumination and in the wavelength range 390 nm-900 nm. The pixels of the colonies that have grown on the agar are extracted, for example in the manner described in steps 46-50 of the method 40, and their associated spectra are stored in the learning database. The latter thus comprises four sets of spectra $\{\gamma_m^Y(\lambda)\}$, $\{\gamma_m^{GP}(\lambda)\}$, $\{\gamma_m^{GNF}(\lambda)\}$, $\{Y_m^{GNN}(\lambda)\}$ associated with the classes Y, GP, GNF, GNN, respectively. Each of these sets is split in two, a first part, called "calibration" being used for the learning proper and a second part, called "cross validation", being used for evaluating the performance of the calculated prediction models, as is known per se from the prior art.

According to a first preferred embodiment, learning carried out by computer, called "step forward", is used for training the prediction models. This type of learning is based on the step by step selection of the most discriminating spectral channels, so that it is intrinsically parsimonious and suitable for finding a multispectral application, as carried out by the system in FIG. 2.

Figure 5:
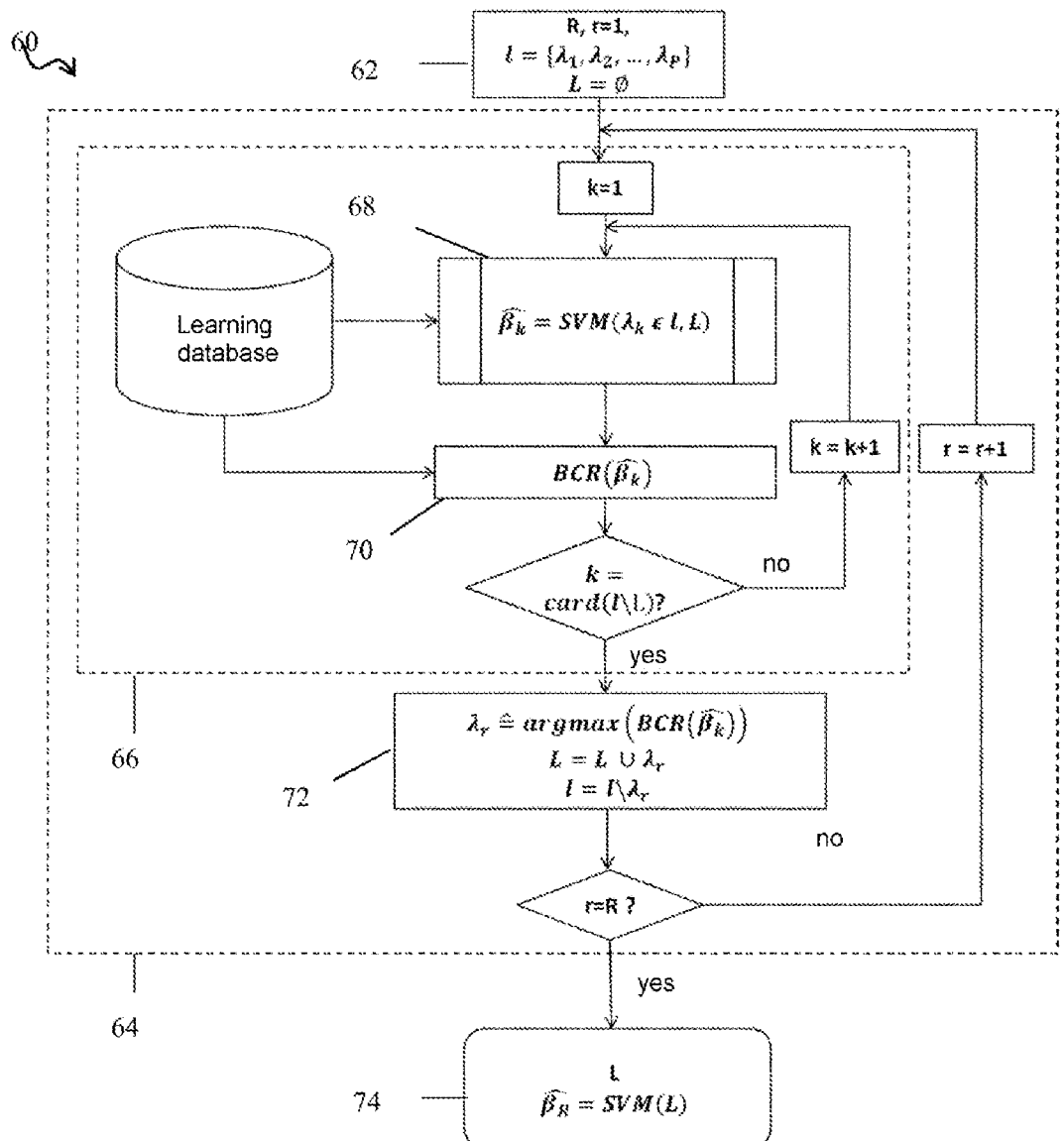
FIG. 5 is a flowchart of a method for selecting discriminating spectral channels by means of the "step forward" approach.

Referring to FIG. 5, learning 60 begins with an initializing step 62 in which a maximum number R of discriminating channels is selected, this number being between 1 and the number P of spectral channels of the hyperspectral camera used for acquisition of the spectra. A list L of the discriminating channels selected is emptied and a list l of the candidate channels is initialized for the set $\{\lambda_1, \lambda_2, \ldots, \lambda_P\}$ of the channels of the hyperspectral camera.

In a following iterative step 64, list l is filled step by step with the most discriminating channels R from the list L using an iterative step 66. More particularly, for a given iteration r of step 64, step 66:

extracts each channel $\lambda_k$ from the list l;
determines, at 68, for the channel extracted $\lambda_k$ and the channels $\{\lambda_1, \lambda_2, \ldots, \lambda_{r-1}\}$ from the list L, a prediction mode $\widehat{\beta_k}$ ;
calculates, at 70, a performance criterion BCR$\widehat{\beta_k}$ ) of the prediction model $\widehat{\beta_k}$ , for example the level of good classification of the spectra in cross validation.

Step 64 then continues, at 72, with identification of the prediction model giving the best performance criterion and consequently identification of the most discriminating channel $\lambda_r$ of the list l in combination with the channels of the list L. At 74, the list L is then completed with the channel $\lambda_r$ and the latter is removed from the list l for the next iteration r+1 of step 64. Once the R most discriminating channels have been identified, the learning process then ends, at 74, with storage of the list L and of the prediction hyperplane $\widehat{\beta_R}$ , $\beta_0^{cl}$ ) associated with the latter, namely the last model identified in step 72.

Advantageously, the prediction models calculated in step 68 are of the SVM type (for "support vector machine"), "one against all", with linear kernel and with soft margin. This type of learning consists of calculating, as a function of the calibration spectra, a hyperplane $\widehat{\beta_k^{Cl}}$ ,$\beta_0^{cl}$) separating a class Cl (Cl=Y, GP, GNF or GNN) of the set Cl formed from one, two or three from among the other classes, as will be described below. For example, the model is trained by solving an optimization problem according to the following relations for an iteration k of step 66 and an iteration r of step 64:

$$\widehat{\beta_k^{Cl}} = \arg\min_{\beta,\xi_m}\left(\frac{1}{2}\|\beta\|^2 + C\sum_{m=1}^{M}\xi_m\right)$$

under the constraints:

$\forall m\in [1,M]{:}\xi_m\geq 0$ $\forall m\in [1,M]{:}q_m(Y_m^{r,k}(\lambda),\beta+\beta_0^{cl})\geq 1-\xi_m$ In the above expressions:
for a calibration spectrum $\gamma_m(\lambda)$ belonging to the class Cl or to the set $\overline{Cl}$, $Y_m^{r,k}(\lambda)$ is equal to the vector of the components of $\gamma_m(\lambda)$ corresponding to the spectral channels of the list L=$\{\lambda_1, \lambda_2, \ldots, \lambda_{r-1}\}$ and of the channel $\lambda_k$ extracted from the list/during the iteration k, preferably a vector whose components are ordinates as a function of the value of the channels;

$\widehat{\beta_k^{Cl}}$ and β are vectors with dimension equal to the dimension of the spectra $\gamma_m^{r,k}(\lambda)$, and consequently of dimension equal to r, M is the number of calibration spectra $\gamma_m(\lambda)$ belonging to the class Cl or to the set Cl, numbered from 1 to M, $\gamma_m^{r,k}(\lambda)$, β is the scalar product of the vector $\gamma_m^{r,k}(\lambda)$ and the vector β, $\tau_m$ and $\beta_0^{cl}$ are scalars;

$q_m\in\{-1,1\}$ with $q_m=1$ if the m-th learning spectrum is associated with the class Cl, and $q_m=-1$ if the m-th spectrum is associated with the set $\overline{Cl}$ of the other classes; and C is a predefined scalar.

The model predicting membership of a spectrum of a pixel $\gamma_{i,j}(\lambda)$ in the class Cl is thus produced according to the following steps:

transformation of the spectrum $\gamma_{i,j}(\lambda)$ into a vector $\gamma_{i,j}^{r,k}(\lambda)$;

calculation of a distance $S_{cl}=Y_{i,j}^{r,k}(\lambda\widehat{\beta_R}}+\beta_0$ between the spectrum $\gamma_{i,j}^{r,k}(\lambda)$ and the hyperplane $\widehat{\beta_K^{Cl}},\beta_0^{cl})$;

application of a rule for predicting the class Cl as a function of the distance $S_{cl}$, for example the spectrum belongs to the class Cl if the sign of $S_{cl}$ is positive, and to the set $\overline{Cl}$ if this sign is negative.

According to a second embodiment, learning is nonparsimonious and consists of using all the channels at the same time, the prediction model resulting therefrom being particularly suitable for a hyperspectral application by means of the system in FIG. 1. For example, this learning is of type SVM, "one against all", with a linear kernel and a soft margin, and consists of calculating, as a function of the calibration spectra, a hyperplane ($\widehat{\beta^{Cl}},\beta_0^{cl}$) separating a class Cl (Cl=Y, GP, GNF or GNN) of the set l formed from one, two or three from among the other classes, by solving an optimization problem according to the relation:

$$\widehat{\beta^{Cl}} = \arg\min_{\beta,\xi_m}\left(\frac{1}{2}\|\beta\|^2 + C\sum_{m=1}^{M}\xi_m\right)$$

under the constraints:

$\forall m\in[1,M]: \xi_m\geq 0$ $\forall m\in[1,M]: q_m(\gamma_m(\lambda).\beta+\beta_0^{cl})\geq 1-\xi_m$ (7)

In these expressions:

$\gamma_m(\lambda)$ is a calibration spectrum $\gamma_m(\lambda)$ belonging to the class Cl or to the set $\overline{Cl}$;

$\widehat{\beta^{Cl}}$ and $\beta$ are vectors with dimension equal to the dimension of the calibration spectra $\gamma_m^{r,k}(\lambda)$, and consequently of dimension equal to P, M is the number of calibration spectra $\gamma_m(\lambda)$ belonging to the class Cl or to the set $\overline{Cl}$, numbered from 1 to M, $\gamma_m(\lambda).\beta$ is the scalar product of the vector $\gamma_m(\lambda)$ times the vector $\beta$, $\xi_m$ and $\beta_0^{cl}$ are scalars;

$q_m\in\{-1,1\}$ with $q_m=1$ if the m-th learning spectrum is associated with the class Cl, and $q_m=-1$ if the m-th spectrum is associated with the set $\overline{Cl}$ of the other classes; and C is a predefined scalar.

The model predicting membership of a spectrum of a pixel $\gamma_{i,j}(\lambda)$ to the class Cl is thus produced according to the following steps:

calculation of a distance $S_{cl}=\gamma_{i,j}(\lambda).\widehat{\beta^{Cl}}+\beta_0^{cl}$ between the spectrum $\gamma_{i,j}(\lambda)$ and the hyperplane ($\widehat{\beta^{Cl}},\beta_0^{cl}$);

application of a rule for predicting the class Cl as a function of the distance $S_{cl}$, for example the spectrum belongs to the class Cl if the sign of $S_{cl}$ is positive, and to the set $\overline{Cl}$ if this sign is negative.

B. Method of Training the Prediction Models

Figure 6:
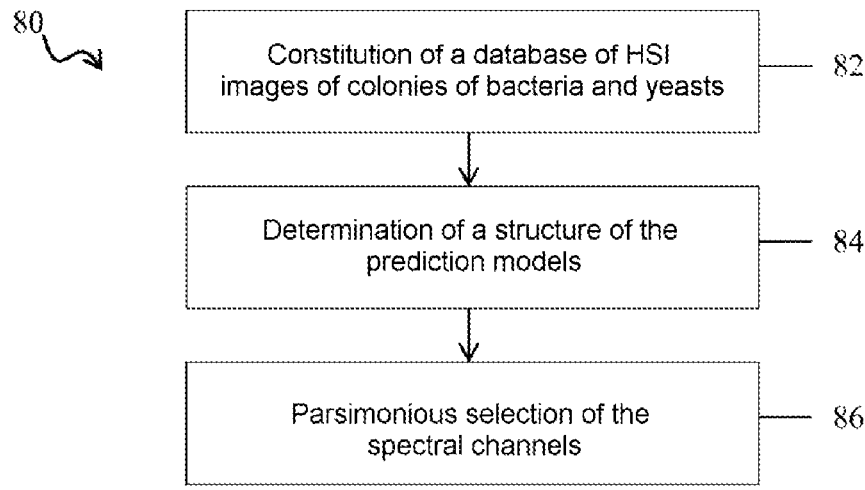
FIG. 6 is a flowchart of a method for learning the models for predicting the classes Y, GP, GNF, GNN.

Referring to FIG. 6, the method 80 for training the prediction models begins with the construction, at 82, of a learning database for the classes Y, GP, GNF and GNN, as described above. The method 80 continues, at 84, with determination of a structure of the prediction models. In particular, two types of model are possible, such as illustrated respectively in FIG. 7A on the one hand and in FIGS. 6B and 6C on the other hand.

Figure 7A:
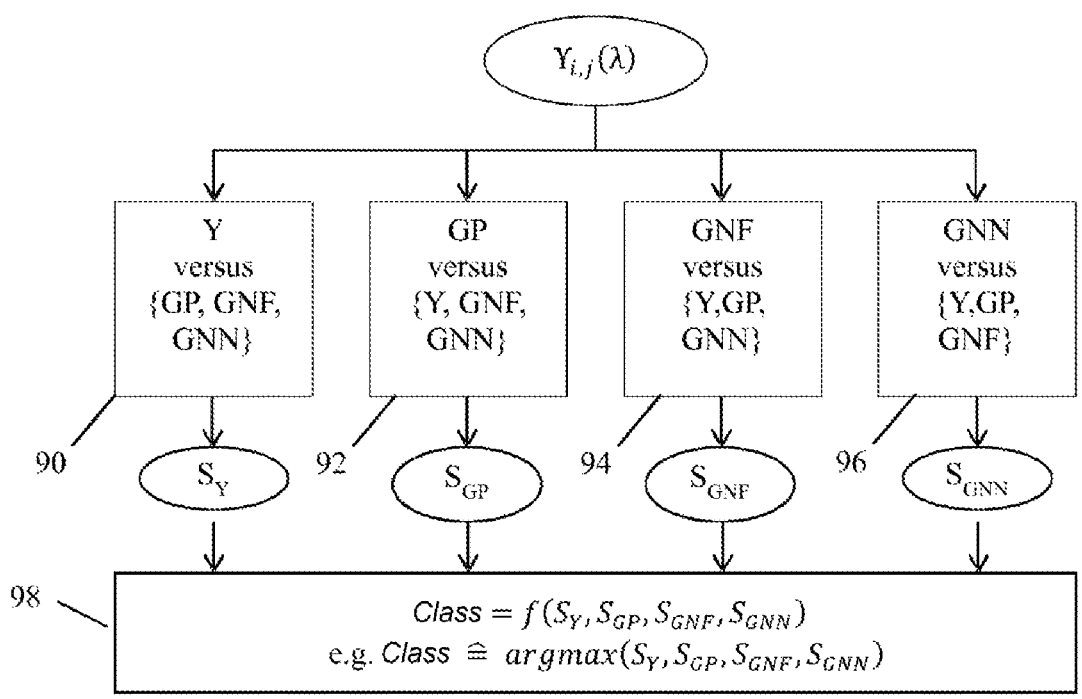
FIG. 7A is a diagram illustrating a flat prediction model for the classes Y, GP, GNF, GNN.

The first type of prediction model, illustrated in FIG. 7A, consists of training four prediction models of the type "one against all" 90, 72, 74, 76, namely a prediction of the class Y versus the classes GP, GNF, GNN, a prediction of the class GP versus the classes Y, GNF, GNN, a prediction of the class GNF versus the classes Y, GP, GNN and a prediction of the class GNN versus the classes Y, GP, GNF. For this purpose:

each prediction model is trained as a function of the learning database using one of the learning tools described above in connection with the relations (6) or (7), the class Cl being equal to Y, GP, GNF GNN and the set $\overline{Cl}$ being made up of the other three classes;

the prediction of the Gram type and fermenting character of a pixel (step 52 in FIG. 3) is obtained by calculating (steps 90-96) the distances $S_Y$, $S_{GP}$, $S_{GNF}$, $S_{GNN}$ of the spectrum $Y_{i,j}(\lambda)$ from said pixel to the hyperplanes $\widehat{\beta_R^Y},\beta_0^Y),\widehat{\beta_R^{GP}},\beta_0^{GP}),\widehat{\beta_R^{GNF}},\beta_0^{GNF}),\widehat{\beta_R^{GNN}},\beta_0^{GNN})$, or to the hyperplanes $\widehat{\beta^Y},\beta_0^Y),\widehat{\beta^{GP}},\beta_0^{GP}),\widehat{\beta^{GNF}},\beta_0^{GNF}),\widehat{\beta^{GNN}},\beta_0^{GNN})$, respectively, and then determining the class of the pixel, at 88, as a function of the calculated distances.

Notably, the class retained is that corresponding to the maximum distance.

According to the first type of structure illustrated in FIG. 7A, called "flat", the classes Y, GP, GNF and GNN are considered to be of equal importance, and consequently the identification errors are as well. For example, identifying a yeast Y in place of a bacterium GNN is as serious as identifying a bacterium GNF in place of a bacterium GNN. According to the structure illustrated in FIG. 7B, the prediction models are organized according to a phylogenetic taxonomic tree, so that the different classes need no longer be considered with equal importance and it becomes possible to introduce information a priori, namely evolution information that may influence the shape of the spectra. More particularly, this prediction model tree comprises:

a first model 100 consisting of distinguishing the yeasts Y from the bacteria GP, GNF, GNF;

a second model 102 consisting of distinguishing the bacteria GP from the bacteria GNF and GNN; and a third model 104 consisting of distinguishing the bacteria GNF from the bacteria GNN.

Each of the models 100-104 is obtained in the manner described above in connection with the relations (6) or (7), and prediction of membership of a spectrum of pixel $Y_{i,j}(\lambda)$ to one of the classes Y, GP, GNF and GNN thus consists of calculating its distance $S_Y$ to the hyperplane of the first model 100 and if the sign of this distance is positive, class Y is then predicted. Otherwise, the distance $S_{GP}$ to the hyperplane of the second model 102 is calculated and if the sign of the latter is positive, then class GP is predicted. Otherwise, the distance $S_{GNF}$ to the hyperplane of the third model 104 is calculated and then class GNF is predicted. Otherwise class GNN is predicted.

Although the phenotypic model makes it possible to improve the prediction accuracy relative to a flat prediction structure as illustrated in FIG. 7A, the inventors noted, however, that the phenotypic tree is not necessarily the tree giving better results. Notably, a tree may be preferred depending on the culture medium on which the microorganisms to be characterized have grown, this medium influencing the shape of the spectra. Preferably, an optimal prediction structure, as illustrated in FIG. 7C, is determined as a function of the calibration spectra. More particularly, in a first step, the four prediction models a) Y versus GP, GNF and GNN, b) GP versus Y, GNF and GNN, c) GNF versus Y, GP and GNN, and d) GNN versus Y, GP and GNF are calculated in the way described above and the model having the best prediction performance is kept as the first model 110 of the optimal tree. In a second step, the class of the first model is removed, and the three prediction models corresponding to the remaining classes are calculated. For example, if the first model corresponds to the class GNN, then the three models of the second step are a) Y versus GP and GNF, b) GP versus Y, and GNF and c) GNF versus Y and GP in the way described above. The best of the three models is then kept as the second model 112 of the optimal tree. In a third step, the classes of the first and second models 110 and 112 are removed, and a prediction model between the two remaining classes is calculated in the way described above and kept as the third model 114 of the optimal tree. Prediction of the membership of a spectrum of pixel $\gamma_{i,j}(\lambda)$ to one of the classes Y, GP, GNF and GNN is then obtained by passing through the tree in a similar way to that described with reference to FIG. 7B.

Returning to FIG. 6, once the structure of the prediction model has been determined, the learning process 80 continues, optionally, at 84, with a decrease in the number of spectral channels used for the prediction, this decrease being made by selection and/or regrouping of channels. In particular, when the prediction models described above with reference to FIGS. 7A, 7B and 7C are calculated on the basis of the "step forward" approach in FIG. 5, the number of channels used may be fixed directly by the parameter R. As a variant, or additionally, the additional channels that do not give a significant increase in the performance of the models may be removed. The regrouping of channels may also be carried out, as a variant or additionally, by dividing the range 390 nm-900 nm into intervals whose width corresponds to that of the filters as described above in connection with FIGS. 2 and 3. A single spectral channel is then retained per interval. A final number of channels Where $\lambda_1, \lambda_2, \ldots, \lambda_{N_F}$ are thus selected and define the central wavelengths of the spectral filters of the set 36 of the multispectral system in FIG. 2. As will be described below, it is possible to obtain a prediction of the classes of high accuracy using only 24 channels, and therefore 24 spectral filters.

Optionally, having selected the final channels for the multispectral application and having constructed the multispectral system correspondingly, a new training operation, based on the acquisition of spectra with the system in FIG. 2, is used for refining the prediction models, this training being similar to that described in connection with FIGS. 6 and 7.

Moreover, selection of a predetermined number R of discriminating channels has been described. As a variant, this number is not fixed a priori and a stop criterion for finding the gaps is stagnation of the gain in performance as a function of the number of channels. If for example addition of at least one channel does not increase the performance, for example BCR detailed below, by more than X %, then the search for channels is stopped, with for example X less than or equal to 2%.

C. Examples

We shall now describe an application of the predictions of the classes Y, GP, GNF and GNN that have just been described. For this purpose, 21 bacterial strains and yeast strains are used, these microbial species being described in FIG. 8. These species were cultured for 24 hours on COS agar and TSA agar, giving rise to a learning database for each of these media. The number of colonies and of pixels for each of the species and media are described in FIG. 9 (COS) and in FIG. 10 (TSA), respectively, block 1 corresponding to the calibration data and block 2 corresponding to the cross validation data.

The performance of prediction of the classes is advantageously calculated as being equal to the average of the sensitivities of the predictions of class (rate of spectra classified well). This weighted criterion, also called "balance classification rate" or "BCR", makes it possible to take account of the sets of pixels that are unbalanced, which is the case on account of the size of the colonies, which is variable as a function of the species. The calculation of BCR is recalled in FIG. 11.

C.1. COS Results

C.1.1. Flat Model

Table 1 below gives the BCRs for a flat prediction model illustrated in FIG. 7A and for prediction models obtained using relations (7).

TABLE 1

| | Calibration | Cross-validation |
|---|---|---|
| Y versus GP + GNN + G NF | 85% | 84% |
| GP versus Y + GNN + GNF | 93% | 91% |
| GNN versus Y + GP + GNF | 80% | 80% |
| GNF versus Y + GP + GNN | 99% | 99% |

It will be noted immediately, on reading Table 1, that the different bacterial strains can be predicted accurately. Notably, knowing that the microorganism to be characterized is a bacterium, it is possible to predict its Gram type and its fermenting or nonfermenting character, using a first prediction GP versus GNN and GNF and a second prediction GNN versus GP and GNF. This type of prediction is particularly useful for the selection of consumables for the performance of an antibiogram with the Vitek®2 platform marketed by the applicant.

C.1.2. Optimal Tree

The BCRs for the models 110, 112, 114 illustrated in FIG. 7C and obtained by means of relations (7) are summarized in Table 2.

TABLE 2

| | Calibration | Cross-validation |
|---|---|---|
| 110: GNF versus Y + GP + GNN | 99% | 99% |
| 112: GP versus Y + GNF | 91% | 90% |
| 114: Y versus GNF | 86% | 84% |

It can be seen that the optimal tree differs markedly from the phylogenetic tree, the influence of the COS medium probably being greater than the influence of phylogenetic differences.

The BCRs of models 110, 112, 114 illustrated in FIG. 7C and obtained using the "step forward" approach in FIG. 4 and relations (6), with R=24 for each of the models, are summarized in Table 3 (see FIG. 21).

It can be seen, on reading Table 3, that the gain in performance is limited starting from the 8th channel for the first model, and from the 4th channel for the third model. To obtain a multispectral application using 24 spectral filters, corresponding to the commercial filter systems, advantageously 8 channels, 14 channels and 4 channels respectively are selected for the first, second and third models 110, 112, 114. The performance figures for this embodiment are summarized in Table 4.

TABLE 4

| | Order of selection of the most discriminating order | Wavelength (nm) | BCR |
|---|---|---|---|
| GNF versus Y + GP + GNN | 1 | 613.58 | 97.10% |
| | 2 | 484.16 | |
| | 3 | 634.45 | |
| | 4 | 605.23 | |
| | 5 | 588.53 | |
| | 6 | 640.71 | |
| | 7 | 607.31 | |
| | 8 | 434.06 | |
| GP versus Y + GNF | 1 | 634.45 | 93.30% |
| | 2 | 598.97 | |
| | 3 | 665.76 | |
| | 4 | 630.28 | |
| | 5 | 864.07 | |
| | 6 | 548.87 | |
| | 7 | 488.33 | |
| | 8 | 628.19 | |
| | 9 | 661.59 | |
| | 10 | 584.35 | |
| | 11 | 530.08 | |
| | 12 | 636.54 | |
| | 13 | 603.14 | |
| | 14 | 486.25 | |
| Y versus GNF | 1 | 613.58 | 95.90% |
| | 2 | 651.15 | |
| | 3 | 425.71 | |
| | 4 | 617.75 | |

Of course, other numbers of channels may be selected depending on the number of spectral filters available for the system in FIG. 2.

Figure 12:
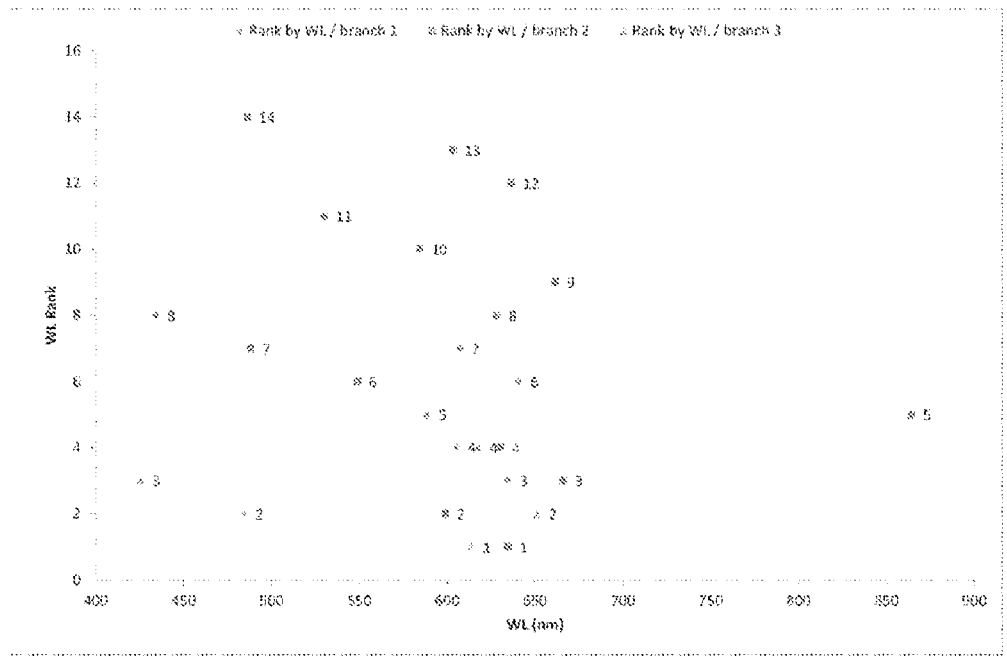
FIG. 12 is a diagram illustrating the spatial distribution of the main discriminating spectral channels for the optimal tree of the COS medium.
Figure 13:
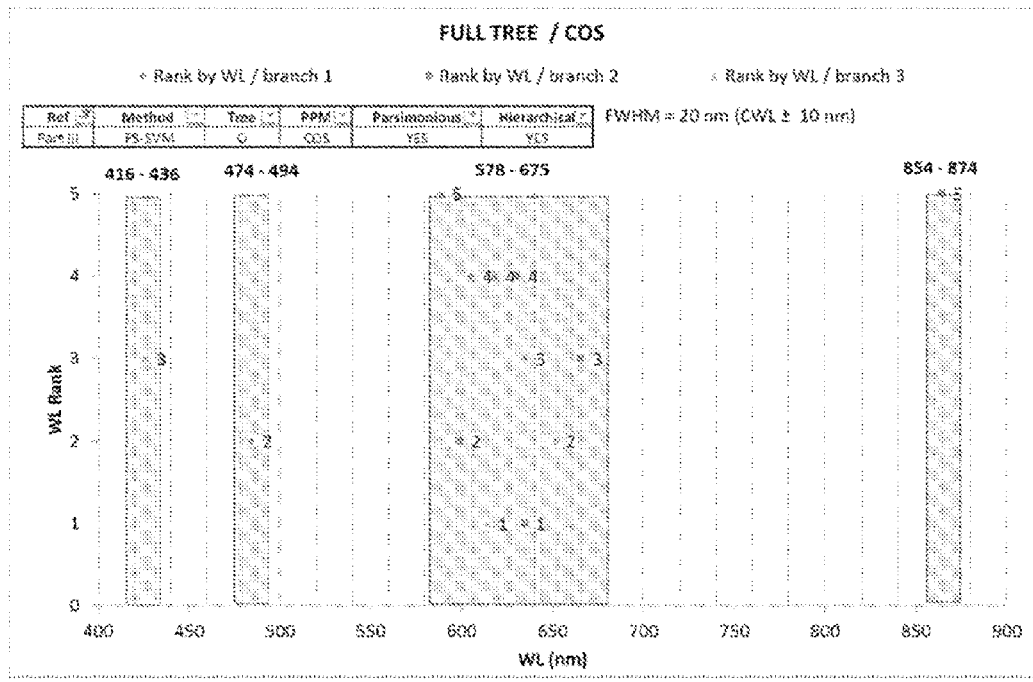
FIG. 13 is a diagram illustrating the spatial distribution of the 5 main discriminating spectral channels of each model for the optimal tree of the COS medium.
Figure 14:
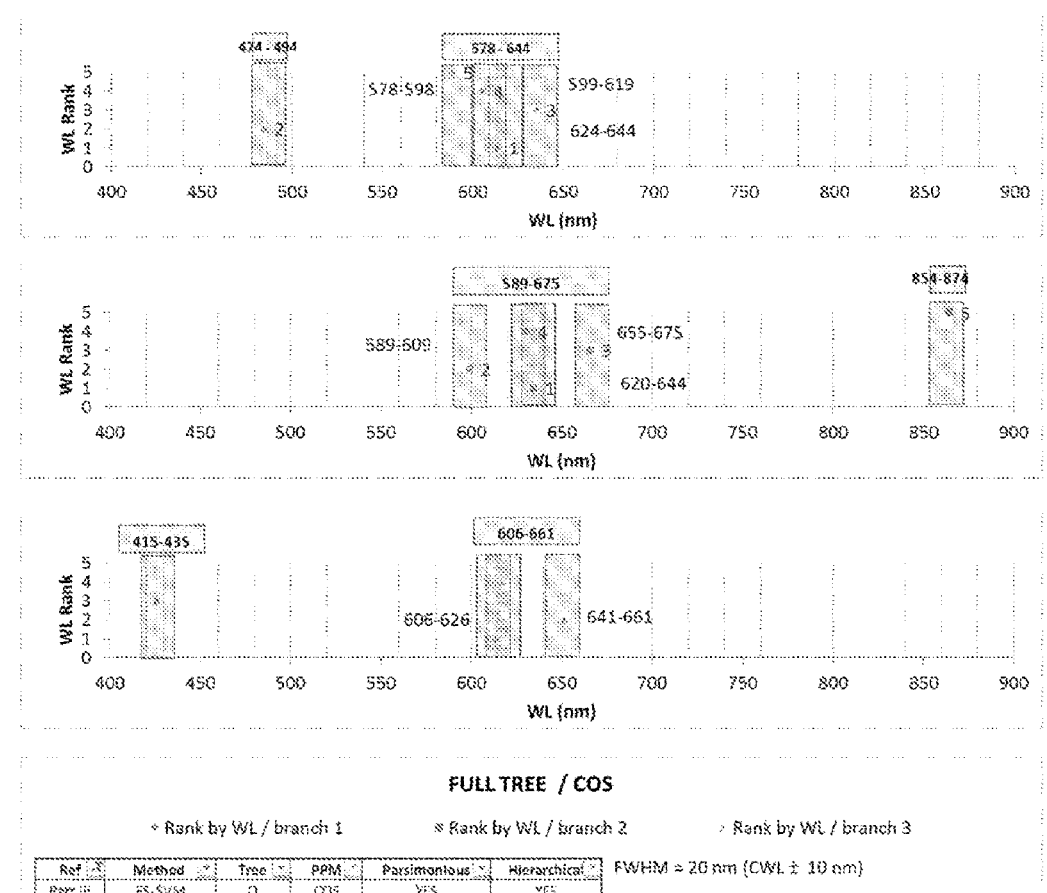
FIG. 14 is a diagram illustrating individually the five main discriminating channels of each model of the optimal tree of the COS medium.

It is noted, moreover, that the "step forward" approach makes it possible to determine the spectral ranges comprising the information necessary for predicting the classes. With limitation to the first five channels of each model, BCRs close to or above 90% are obtained, respectively. The spectral distribution of these channels is illustrated in FIGS. 12 to 14. Thus, distinct spectral 10 bands more than 50 nm apart can be distinguished. In particular:

- A. the four classes Y, GP, GNF and GNN can be predicted efficiently using only the spectral data in a first range 415-500 nm and a second range 535-675 nm. Using only these ranges, the BCRs are greater than or equal to 90%. By limiting the first range to 575-675 nm, only 4 channels are used per model for BCRs close to or above 90%. Optionally, a third range 850-875 nm, corresponding to the channel of rank 5 of the second model, is used. More particularly, the prediction in the first range 415-500 nm may be based solely on the ranges 415-440 nm and 470-495 nm. The invention thus covers any method for predicting the classes Y, GP, GNF and GNN consisting of acquiring spectra in said ranges and predicting the classes as a function of said spectra solely in said ranges. It is noted, moreover, that if the invention makes it possible to distinguish between the classes Y, GP, GNF and GNN, it therefore makes it possible to distinguish between yeasts and bacteria, based on the spectral data contained in the aforementioned ranges. The invention therefore also covers a method for predicting the yeast or bacterial character of a microorganism to be characterized;
- B. prediction of the class GNF versus Y+GP+GNN may be carried out efficiently solely on a first range 470-500 nm and a second range 575-645 nm. The invention thus covers any method for predicting the class GNF consisting of acquiring the spectra in said ranges and predicting the class GNF as a function of said spectra solely in said ranges. It should be noted that when the bacterial character of the microorganism to be characterized is already known, the prediction then consists of predicting the class GNF versus GP and GNN. The invention therefore also covers this type of prediction based solely on the ranges 470-500 nm and 575-645 nm;
- C. prediction of the class GP versus Y+GNN may be carried out efficiently solely on the first range 535-675 nm, and more particularly on the range 585-675 nm, and the second range 850-875 nm. The invention thus covers any method for predicting the class GP consisting of acquiring the spectra in said ranges and predicting the class GP as a function of said spectra solely in said ranges. It should be noted that when the bacterial character of the microorganism to be characterized is already known, prediction then consists of predicting the class GP versus the classes GNF and GNN, and consequently by the class GP versus the class of the Gram-negative bacteria (GN). The invention therefore also covers this type of prediction based solely on the ranges 535-675 nm, and more particularly on the range 585-675 nm, and the range 850-875 nm;
- D. On combining the predictions described in points B and C below, it can thus be seen that with three ranges, and knowing the bacterial character of the microorganism to be characterized, it is possible to determine whether a bacterial colony is GP, GNF or GNN. This type of prediction is notably useful for selecting consumables for generating an antibiogram with the Vitek®2 platform marketed by the applicant.

C.1.3. Phylogenetic Tree

Figure 7B:
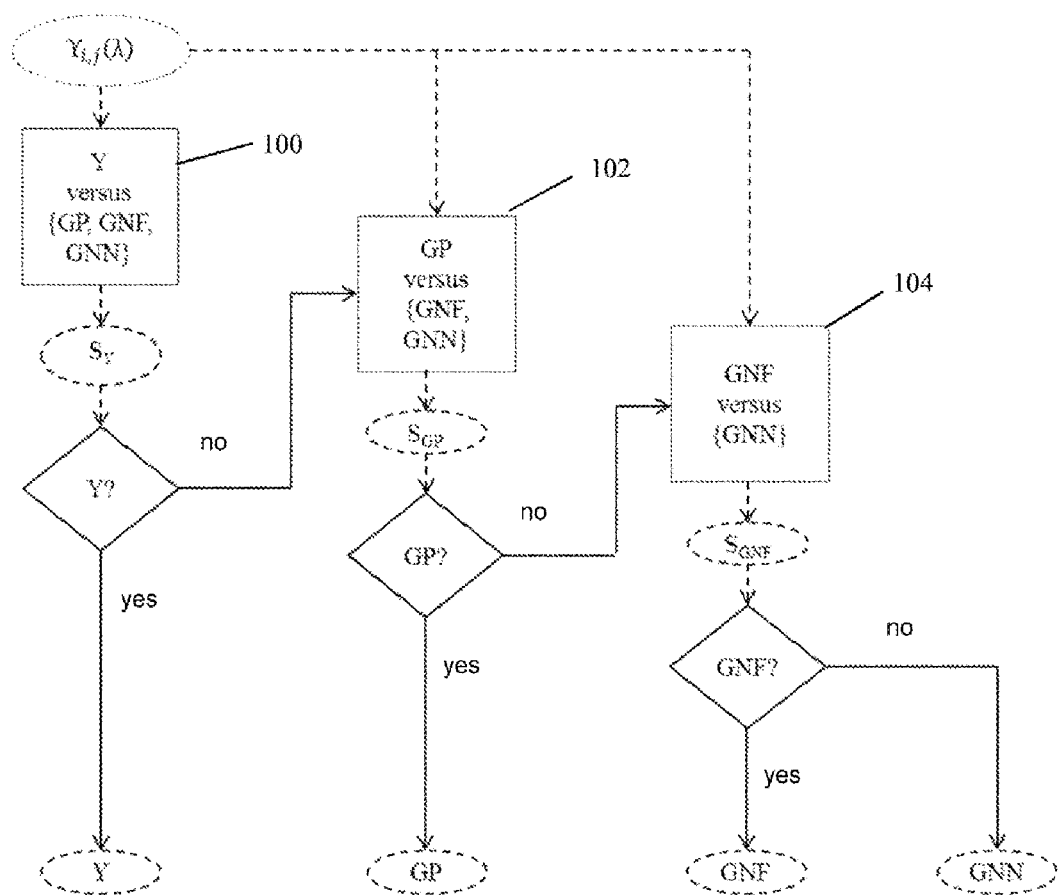
FIG. 7B is a diagram illustrating a hierarchical prediction model according to a phylogenetic tree of the classes Y, GP, GNF, GNN.
Figure 7C:
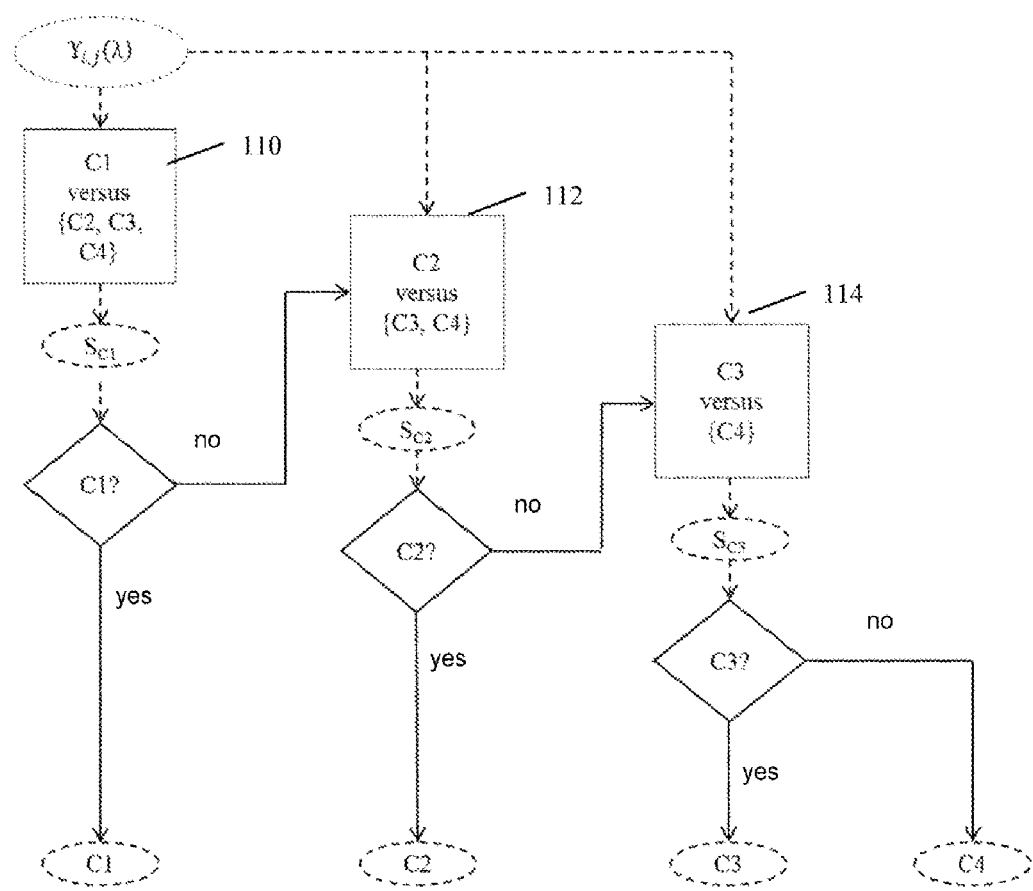
FIG. 7C is a diagram illustrating a hierarchical prediction model according to an optimal tree of the classes Y, GP, GNF, GNN.

The BCRs of models 100, 102, 104 illustrated in FIG. 7B and obtained by means of relations (7) are summarized in Table 5.

TABLE 5

| | Calibration | Cross-validation |
|---|---|---|
| 100: Y versus GP + GNN + GNF | 85% | 84% |
| 102: GP versus GNN + GNF | 95% | 96% |
| 104: GNF versus GNN | 97% | 97% |

C.2. TSA Results

C.2.1. Flat Model

Table 1 below gives the BCRs for a flat prediction model illustrated in FIG. 7A and for prediction models obtained by means of relations (7).

TABLE 6

| | Calibration | Cross-validation |
|---|---|---|
| Y versus GP + GNN + GNF | 89% | 88% |
| GP versus Y + GNN + GNF | 91% | 90% |
| GNN versus Y + GP + GNF | 75% | 73% |
| GNF versus Y + GP + GNN | 90% | 88% |

C.2.2. Optimal Tree

The BCRs of models 110, 112, 114 illustrated in FIG. 7C and obtained by means of relations (7) are summarized in Table 7.

TABLE 7

|  | Calibration | Cross-validation |
|---|---|---|
| 110: GP versus Y + GNF + GNN | 91% | 90% |
| 112: Y versus GNF + GNN | 94% | 93% |
| 114: GNF versus GNN | 82% | 81% |

It can be seen that the optimal tree differs markedly from the phylogenetic tree, the influence of the COS medium probably being greater than the influence of phylogenetic differences.

The BCRs of models 110, 112, 114 illustrated in FIG. 7C and obtained by means of the "step forward" approach in FIG. 5 and relations (6), with R=24 for each of the models, are summarized in Table 8 (see FIG. 22).

Figure 15:
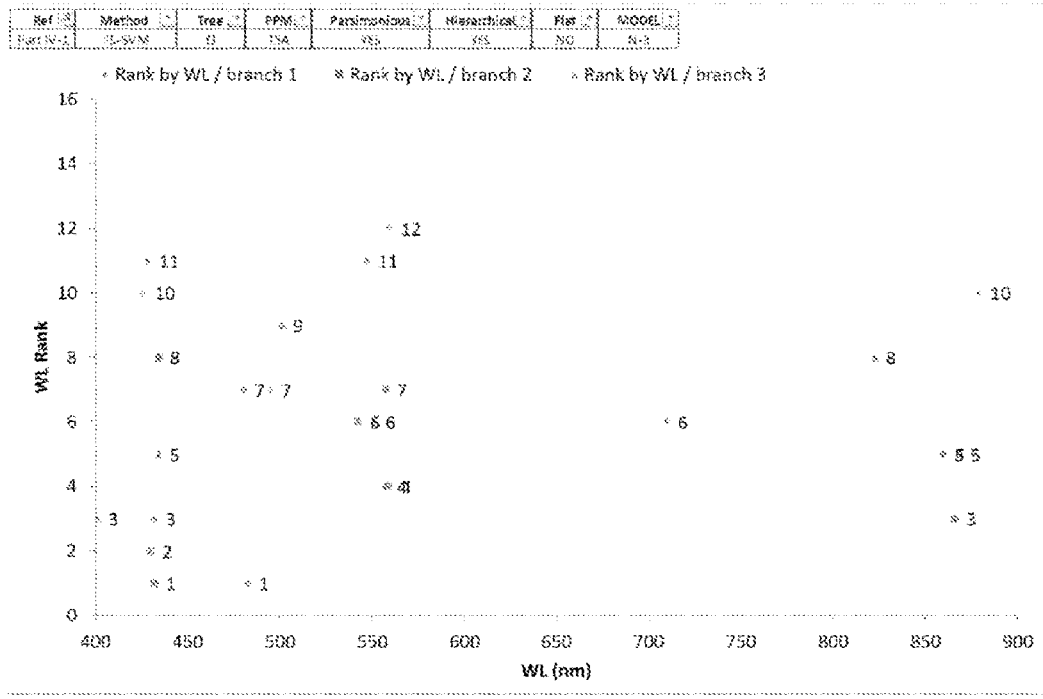
FIG. 15 is a diagram illustrating the spatial distribution of the main discriminating spectral channels for the optimal tree of the TSA medium.
Figure 16:
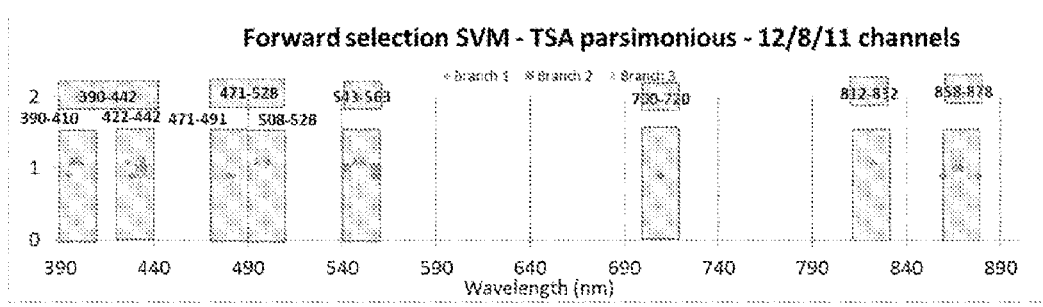
FIG. 16 is a diagram illustrating the spatial distribution of the main discriminating spectral channels for the optimal tree of the COS medium.
Figure 17:
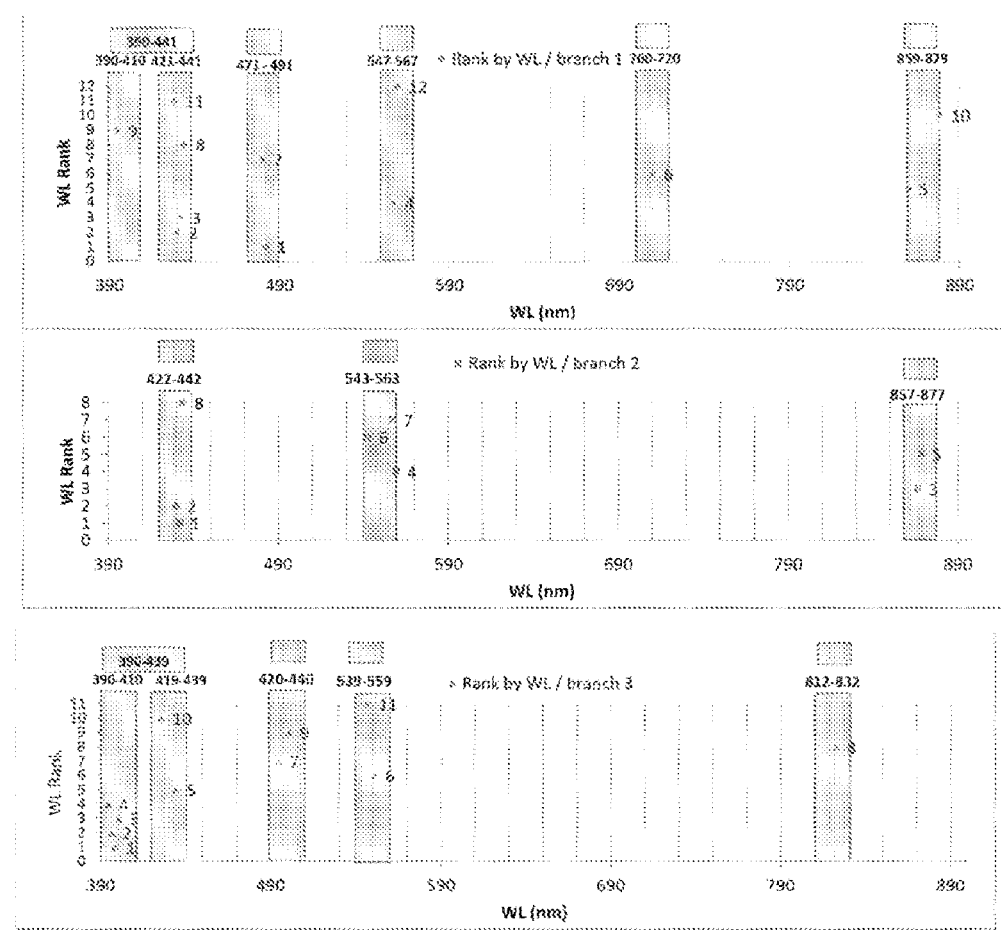
FIG. 17 is a diagram illustrating respectively the 12, 8 and 11 main discriminating channels associated respectively with the first, second and third prediction model of the optimal tree of the TSA medium.

FIGS. 15 to 17 illustrate the spectral distribution of the principal channels of the branches, in one and the same diagram (FIG. 15), in a parsimonious approach with 12, 8 and 11 channels for the first, second and third models 110, 112 and 114, (FIG. 16) and per model (FIG. 17).

C.2.3. Phylogenetic Tree

The BCRs of models 100, 102, 104 illustrated in FIG. 7B and obtained by means of relations (7) are summarized in Table 9.

TABLE 9

|  | Calibration | Cross-validation |
|---|---|---|
| 100: Y versus GP + GNN + GNF | 89% | 88% |
| 102: GP versus GNN + GNF | 92% | 92% |
| 104: GNF versus GNN | 82% | 81% |

The BCRs of models 100, 102, 104 illustrated in FIG. 7B and obtained by means of the "step forward" approach in FIG. 4 and relations (6), with R=24 for each of the models, are summarized in Table 10 (see FIG. 23).

Figure 18:
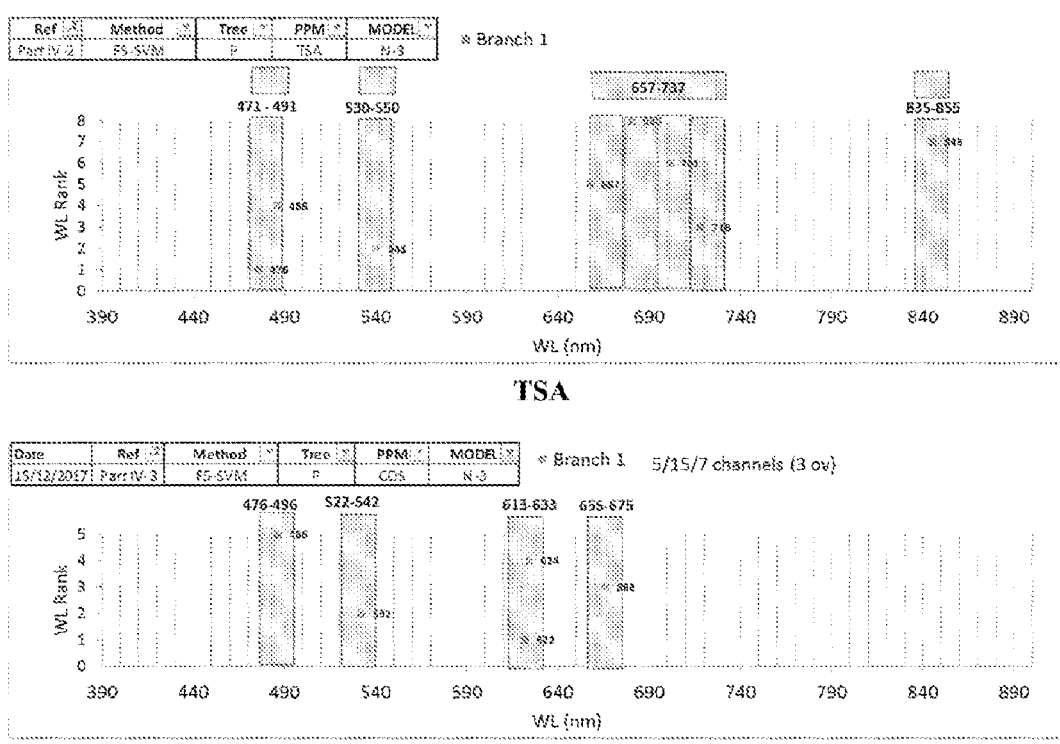
FIGS. 18 to 20 are diagrams illustrating respectively the first, second and third prediction models of the phylogenetic tree, the diagram at the top of each figure corresponding to the TSA medium and the diagram at the bottom of each figure corresponding to the COS medium.
Figure 19:
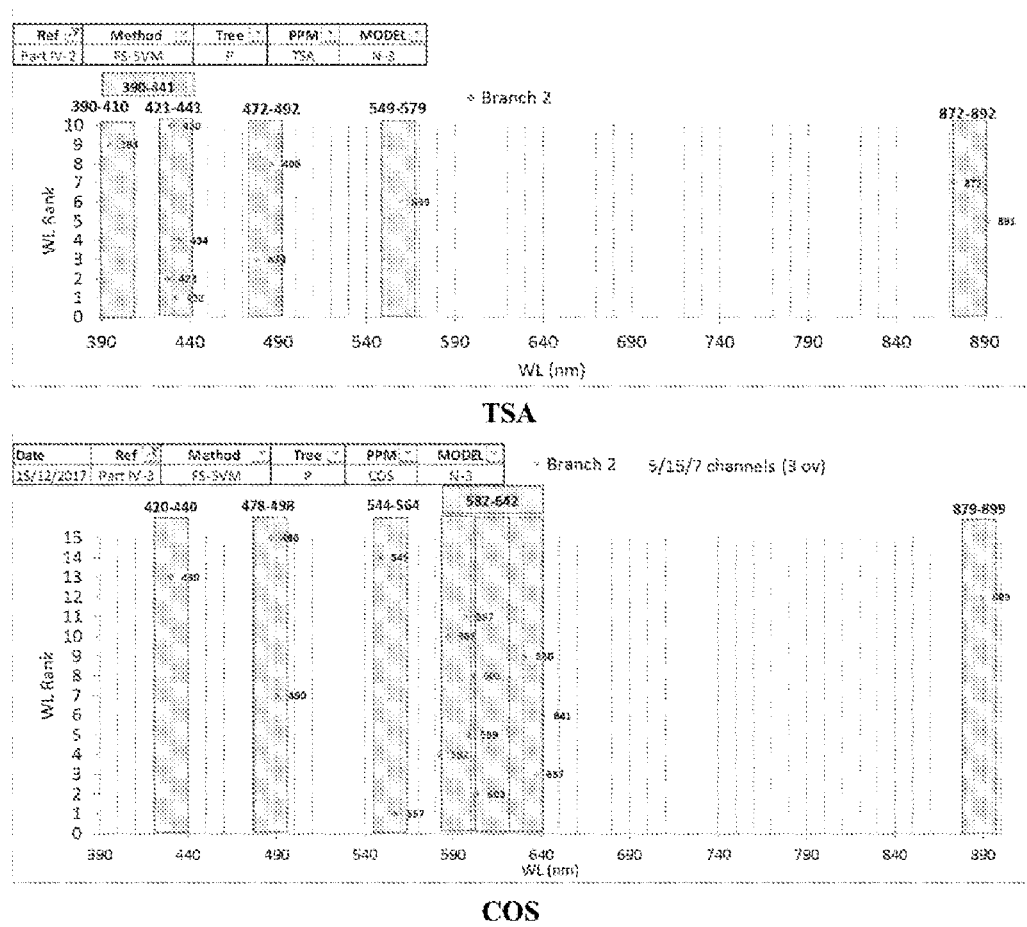
Figure 20:
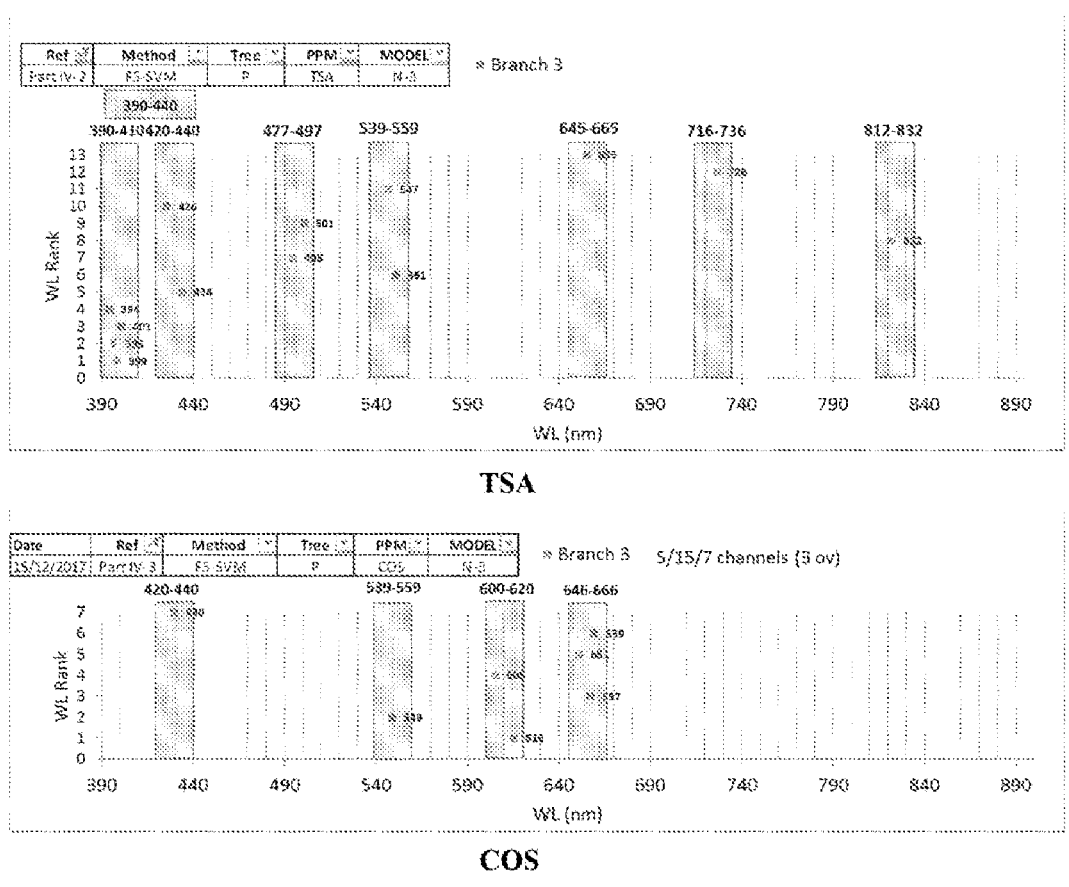

FIGS. 18 to 20 illustrate the spectral distribution of the main spectral channels, model by model, with the TSA medium at the top of each of these figures and in comparison with the COS medium at the bottom of each of the figures.

The invention claimed is:

1. A method for characterizing a microorganism, comprising:
   illuminating, in a wavelength range 390 nm-900 nm, the microorganism having a natural electromagnetic response in the range, wherein the illuminating covers one or more wavelength ranges, wherein the one or more wavelength ranges cover at least two distinct spectral bands whose center wavelengths are more than 50 nm apart;
   acquiring, in the range, a luminous intensity reflected by, or transmitted through, the illuminated microorganism; and
   determining the microorganism from the at least two distinct spectral bands whose center wavelengths are more than 50 nm apart as being a yeast or a bacterial strain, as a function of the luminous intensity acquired in the range, by applying an automated prediction model,
   wherein the prediction model includes at least one class identifying the luminous intensity as belonging to a yeast and at least one class identifying the luminous intensity as belonging to a bacterial strain,
   wherein the prediction model does not include a class identifying the microorganism at a species level.

2. The method as claimed in claim 1, further comprising detection of the Gram type and of the fermenting character of a bacterial strain, comprising determining the microorganism as being a bacterial strain as a function of the luminous intensity acquired in the range, and further determining the Gram type and the fermenting character of the bacterial strain as a function of the luminous intensity acquired in the range.

3. The method as claimed in claim 2, in which the determination of the Gram type and fermenting character comprises applying a first classification of the prediction model predicting whether the luminous intensity acquired is the luminous intensity of a bacterial strain of the Gram-negative type and fermenting.

4. The method as claimed in claim 3, in which:
   illumination and acquisition are carried out directly on a sample comprising a colony of the bacterial strain and a culture medium on which the colony has grown, the culture medium being a blood agar;
   if the luminous intensity acquired is not the luminous intensity of a bacterial strain of the Gram-negative type and fermenting, the determination of the Gram type and fermenting character further comprises applying a second classification of the prediction model predicting whether the luminous intensity acquired is that of a bacterial strain of the Gram-positive type.

5. The method as claimed in claim 4, in which, if the luminous intensity acquired is not the luminous intensity of a bacterial strain of the Gram-positive type, the determination of the Gram type and fermenting character further comprises applying a third classification of the prediction model predicting whether the luminous intensity acquired is the luminous intensity of a yeast.

6. The method as claimed in claim 5, in which:
   the first classification predicting whether the luminous intensity acquired is the luminous intensity of a bacterial strain of the Gram-negative type and fermenting is a classification distinguishing the luminous intensity of the bacterial strains of the Gram-negative type and fermenting from the luminous intensity of the set made up of the bacterial strains of the negative type and nonfermenting, bacterial strains of the Gram-positive type and yeasts;
   the second classification predicting whether the luminous intensity acquired is the luminous intensity of a bacterial strain of the Gram-positive type is a classification distinguishing the luminous intensity of the bacterial strains of the Gram-positive type from the luminous intensity of the set made up of the bacterial strains of the negative type and nonfermenting and yeasts;
   the third classification predicting whether the luminous intensity acquired is the luminous intensity of a yeast is a classification distinguishing the luminous intensity of the yeasts from the luminous intensity of the set made up of the bacterial strains of the Gram-negative type and nonfermenting.

7. The method as claimed in claim 3, in which each classification is trained on hyperspectral images in the range 390 nm-900 nm and according to an approach comprising increasing step-by-step a set of spectral channels used in the classification until a threshold of predetermined accuracy or a predetermined maximum number of channels is obtained.

8. The method as claimed in claim 3, in which the first classification distinguishes between the luminous intensities as a function of the wavelength range 470 nm-500 nm and of the wavelength range 575-645 nm only.

9. The method as claimed in claim 4, in which the second classification distinguishes between the luminous intensities as a function of the wavelength range 415 nm-500 nm and of the wavelength range 535 nm-675 nm only.

10. The method as claimed in claim 4, in which the luminous intensity is acquired on a number of spectral channels less than or equal to 5 for each of the first and second classifications.

11. The method as claimed in claim 2, in which the determination of the Gram type and fermenting character comprises applying at least one selected from the group consisting of:
- a classification of the prediction model predicting whether the luminous intensity acquired is the luminous intensity of a bacterial strain of the Gram-positive type, and
- another classification of the prediction model predicting whether the luminous intensity acquired is the luminous intensity of a bacterial strain of the Gram-negative type.

12. The method as claimed in claim 11, in which:
- illumination and acquisition are carried out directly on a sample comprising a colony of the bacterial strain and a culture medium on which said colony has grown, the culture medium being a tryptone-soy agar;
- if the luminous intensity acquired is not the luminous intensity of a bacterial strain of the Gram-positive type, determination of the Gram type and fermenting character further comprises applying a classification predicting whether the luminous intensity acquired is the luminous intensity of a yeast.

13. The method as claimed in claim 12, in which, if the luminous intensity acquired is not the luminous intensity of a yeast, determination of the Gram type and fermenting character further comprises applying a classification predicting whether the luminous intensity is the luminous intensity of a bacterial strain of the Gram-negative type and fermenting or of a bacterial strain of the Gram-negative type and nonfermenting.

14. The method as claimed in claim 13, in which:
- the classification predicting whether the luminous intensity is the luminous intensity of a bacterial strain of the Gram-positive type is a classification distinguishing the luminous intensity of the bacterial strains of the Gram-positive type from the luminous intensity of the set made up of the bacterial strains of the Gram-negative type and nonfermenting, the bacterial strains of the Gram-negative type and fermenting, and the yeasts;
- the classification predicting whether the luminous intensity acquired is the luminous intensity of yeast is a classification distinguishing the luminous intensity of the yeasts from the intensity of the set made up of the bacterial strains of the negative type and nonfermenting and the bacterial strains of the negative type and fermenting;
- the classification whether the luminous intensity is the luminous intensity of a bacterial strain of the Gram-negative type and fermenting or of a bacterial strain of the Gram-negative type and nonfermenting is a classification distinguishing the luminous intensity of the bacterial strains of the Gram-negative type and nonfermenting from the luminous intensity of the group made up of the bacterial strains of the Gram-negative type and fermenting.

15. The method as claimed in claim 11, in which the applied classification distinguishes between the luminous intensities as a function of the wavelength range 535 nm-675 nm and of the wavelength range 850 nm-875 nm only.

16. The method as claimed in claim 2, comprising applying a classification of the prediction model predicting that the luminous intensity acquired is not the luminous intensity of a yeast, wherein the determination of the Gram type and fermenting character comprises applying a classification of the prediction model predicting whether the luminous intensity acquired is the luminous intensity of a bacterial strain of the Gram-positive type.

17. The method as claimed in claim 16, in which, if the luminous intensity acquired is not the luminous intensity of a bacterial strain of the Gram-positive type, determination of the Gram type and fermenting character further comprises applying a classification of the prediction model predicting whether the luminous intensity is the luminous intensity of a bacterial strain of the Gram-negative type and fermenting or of a bacterial strain of the Gram-negative type and nonfermenting.

18. The method as claimed in claim 17, in which:
- the classification predicting whether the luminous intensity acquired is the luminous intensity of a yeast is a classification distinguishing the luminous intensity of the yeasts from the luminous intensity of the set made up of the bacterial strains of the Gram-positive type, the bacterial strains of the Gram-negative type and nonfermenting, and the bacterial strains of the Gram-negative type and fermenting;
- the classification predicting whether the luminous intensity is the luminous intensity of a bacterial strain of the Gram-positive type is a classification distinguishing the luminous intensity of the bacterial strains of the Gram-positive type from the luminous intensity of the set made up of the bacterial strains of the Gram-negative type and nonfermenting and the bacterial strains of the Gram-negative type and fermenting;
- the classification whether the luminous intensity is the luminous intensity of a bacterial strain of the Gram-negative type and fermenting or of a bacterial strain of the Gram-negative type and nonfermenting is a classification distinguishing the luminous intensity of the bacterial strains of the Gram-negative type and nonfermenting from the luminous intensity of the group made up of the bacterial strains of the Gram-negative type and fermenting.

19. The method as claimed in claim 1, in which the luminous intensity is acquired on a number of spectral channels less than or equal to 24.

20. The method as claimed in claim 1, in which the acquiring of the luminous intensity comprises:
- acquiring a hyperspectral or multispectral image of a colony of bacterium of the strain, and
- determining the luminous intensity as a function of at least one pixel of the image corresponding to the colony.

21. The method as claimed in claim 20, in which the determining of the microorganism as being a yeast or a bacterial strain, as a function of the luminous intensity acquired in the range, by applying the automated prediction model, comprises:
- carrying out, for each pixel of a set of pixels of the colony, a respective first prediction of the Gram type and fermenting character as a function of the luminous intensity of the respective pixel, and
- determining the Gram type and the fermenting character by a majority vote of the results of the first predictions.

22. The method as claimed in claim 21, in which the majority vote is a vote at 70% of the pixels or more.

23. A system for characterization of a microorganism, comprising:
- an illumination device configured for illuminating the microorganism in a wavelength range 390 nm-900 nm, wherein the illuminating by the illuminating device covers one or more wavelength ranges, wherein the one or more wavelength ranges cover at least two distinct spectral bands whose center wavelengths are more than 50 nm apart;
- a sensor configured for acquiring, in the range 390 nm-900 nm, a luminous intensity reflected by, or transmitted through, the illuminated microorganism; and
- a computer unit configured for determining the microorganism from the at least two distinct spectral bands whose center wavelengths are more than 50 nm apart as being a yeast or a bacterial strain as a function of the luminous intensity acquired in the range, by applying an automated prediction model,
- wherein the prediction model includes at least one class identifying the luminous intensity as belonging to a yeast and at least one class identifying the luminous intensity as belonging to a bacterial strain,
- wherein the prediction model does not include a class identifying the microorganism at a species level.

24. The system as claimed in claim 23, configured for implementing a method for characterizing a microorganism, comprising determining the microorganism as being a bacterial strain as a function of the luminous intensity acquired in the range, and further determining the microorganism as being a yeast or a bacterial strain, as a function of the luminous intensity acquired in the range;

the method further comprising detection of the Gram type and of the fermenting character of a bacterial strain, comprising:
- illuminating, in a wavelength range 390 nm-900 nm, at least one bacterium of the strain having a natural electromagnetic response in the range, wherein the illuminating covers one or more wavelength ranges, wherein the one or more wavelength ranges cover at least two distinct spectral bands whose center wavelengths are more than 50 nm apart;
- acquiring, in the range, a luminous intensity reflected by, or transmitted through, the illuminated bacterium; and
- determining the Gram type and the fermenting character of the bacterial strain as a function of the luminous intensity acquired in the range.

25. The system as claimed in claim 23, configured for illuminating, and acquiring the image of, a sample comprising a colony of microorganisms and a culture medium on which the colony has grown.

* * * * *